(12) United States Patent
Tsukamoto et al.

(10) Patent No.: US 9,645,145 B2
(45) Date of Patent: May 9, 2017

(54) SENSOR CHIP, DETECTION SYSTEM, AND METHOD OF DETECTING TARGET SUBSTANCE IN ANALYTE

(71) Applicant: TOHOKU UNIVERSITY, Sendai-shi, Miyagi (JP)

(72) Inventors: Takashiro Tsukamoto, Sendai (JP); Shuji Tanaka, Sendai (JP); Tomohiro Ishikawa, Sendai (JP)

(73) Assignee: TOHOKU UNIVERSITY, Sendai-Shi (JP)

( * ) Notice: Subject to any disclaimer, the term of this patent is extended or adjusted under 35 U.S.C. 154(b) by 0 days.

(21) Appl. No.: 14/667,249

(22) Filed: Mar. 24, 2015

(65) Prior Publication Data

US 2016/0169883 A1   Jun. 16, 2016

(30) Foreign Application Priority Data

Dec. 12, 2014   (JP) .................................. 2014-251602

(51) Int. Cl.
*G01N 27/403*      (2006.01)
*G01N 33/543*      (2006.01)

(52) U.S. Cl.
CPC ....... *G01N 33/5438* (2013.01); *G01N 27/403* (2013.01)

(58) Field of Classification Search
None
See application file for complete search history.

(56) References Cited

U.S. PATENT DOCUMENTS

| 2009/0124024 A1 | 5/2009 | Kasai et al. |
| 2009/0159458 A1 | 6/2009 | Tamiya et al. |
| 2009/0179503 A1 | 7/2009 | Yoshioka et al. |
| 2012/0062379 A1 | 3/2012 | Hafezi et al. |
| 2012/0213669 A1 | 8/2012 | Kasai et al. |
| 2014/0105789 A1 | 4/2014 | Kasai et al. |

FOREIGN PATENT DOCUMENTS

| JP | 2003-534671 A | 11/2003 |
| JP | 2008-096426 A | 4/2008 |
| JP | 2009-133842 A | 6/2009 |
| JP | 2009-170262 A | 7/2009 |
| JP | 2009-240474 A | 10/2009 |
| JP | 2014-525780 A | 10/2014 |

(Continued)

OTHER PUBLICATIONS

Kimura et al., "Fundamental constitution of on-chip microbattery for disposable immuno-sensor chip", published Oct. 13, 2014, with English abstract.

(Continued)

*Primary Examiner* — Rebecca Martinez
(74) *Attorney, Agent, or Firm* — Myers Wolin, LLC

(57) ABSTRACT

A sensor chip includes first and second electrodes that are exposed from the sensor chip and are made from materials different from each other. The sensor chip further includes a detection circuit that detects a target substance included in an analyte, the detection circuit being driven by a potential difference between the first and second electrodes, the potential difference being generated by an oxidation at the first electrode and a reduction at the second electrode while the analyte contacts the first and second electrodes, the analyte including an electrolyte.

20 Claims, 31 Drawing Sheets

(56) References Cited

FOREIGN PATENT DOCUMENTS

WO          00/48338 A1     8/2000
WO     2007/116811 A1   10/2007

OTHER PUBLICATIONS

Kimura et al., "PowerPoint Presentation Material of Fundamental constitution of on-chip microbattery for disposable immuno-sensor chip", published Oct. 20, 2014.
Aytur et al., "A 2.2-mm2 CMOS Bioassay Chip and Wireless Interface", IEEE, 2004 Symposium on VLSI Circuits Digest of Technical Papers, Jun. 2004, pp. 314-317.
Ishikawa et al., "ImmunoSensor" Berkeley Sensor & Actuator Center Dept. of Electrical Engineering and Computer Sciences UCBerkeley, BSAC Copyright 2004.
Aytur, "A CMOS Biosensor for Infectious Disease Detection", Electric Engineering and Computer Sciences University of California at Berkeley, Technical Report No. UCB/EECS-2007-108, published Aug. 24, 2007.

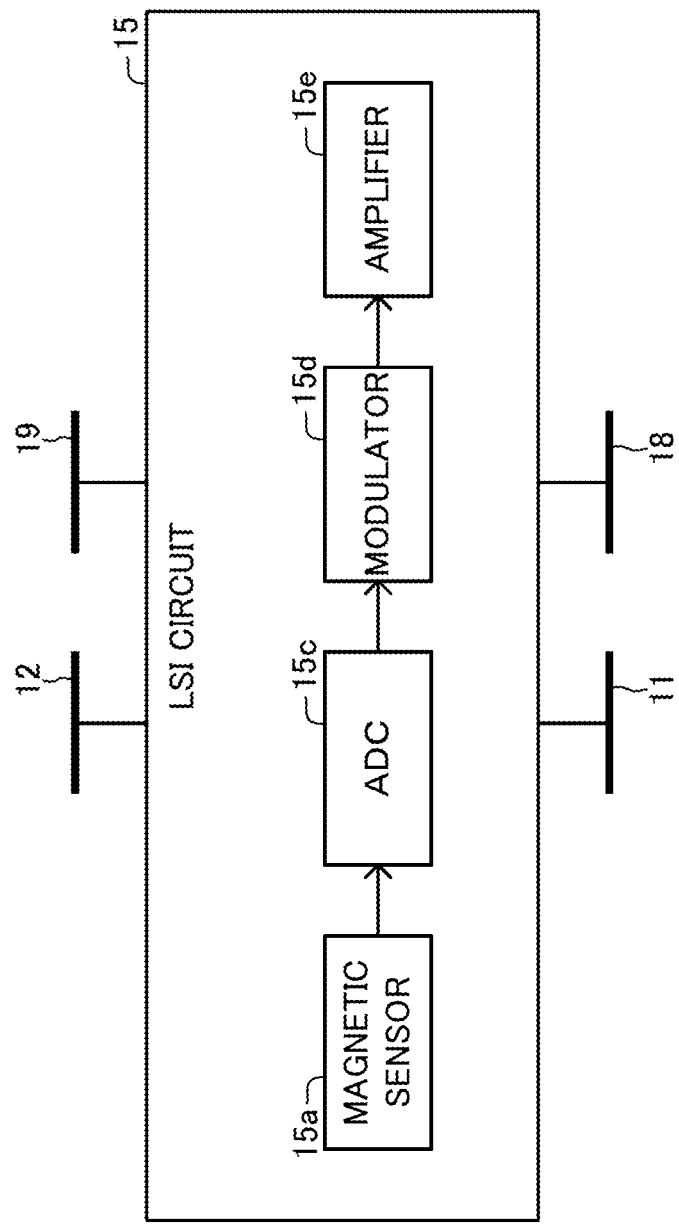

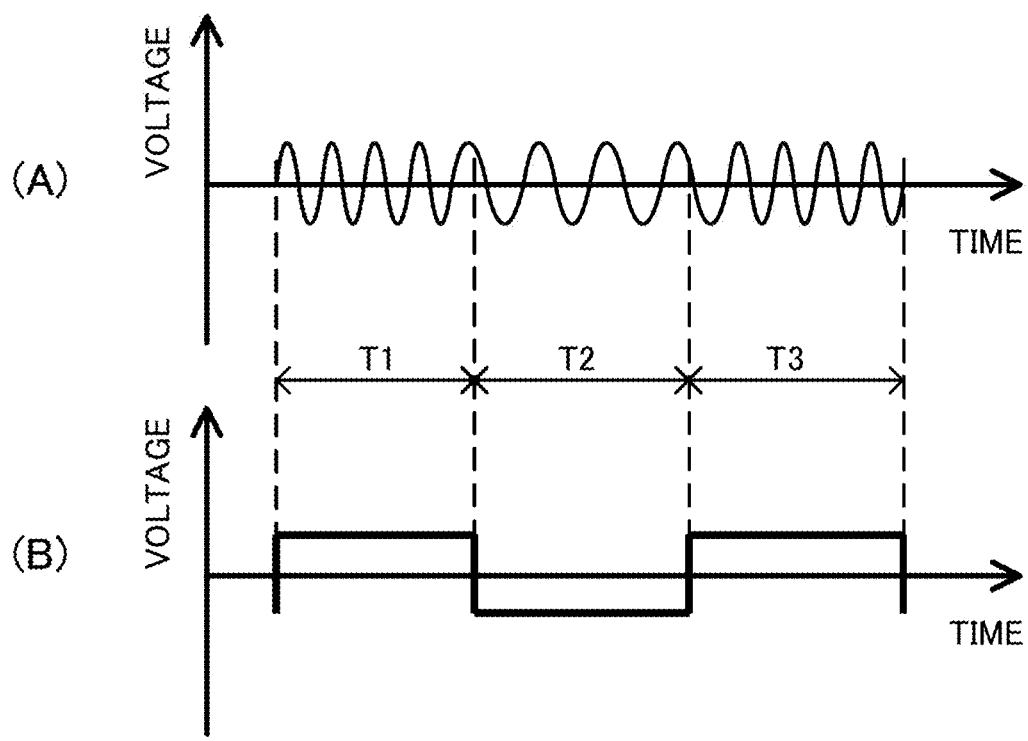

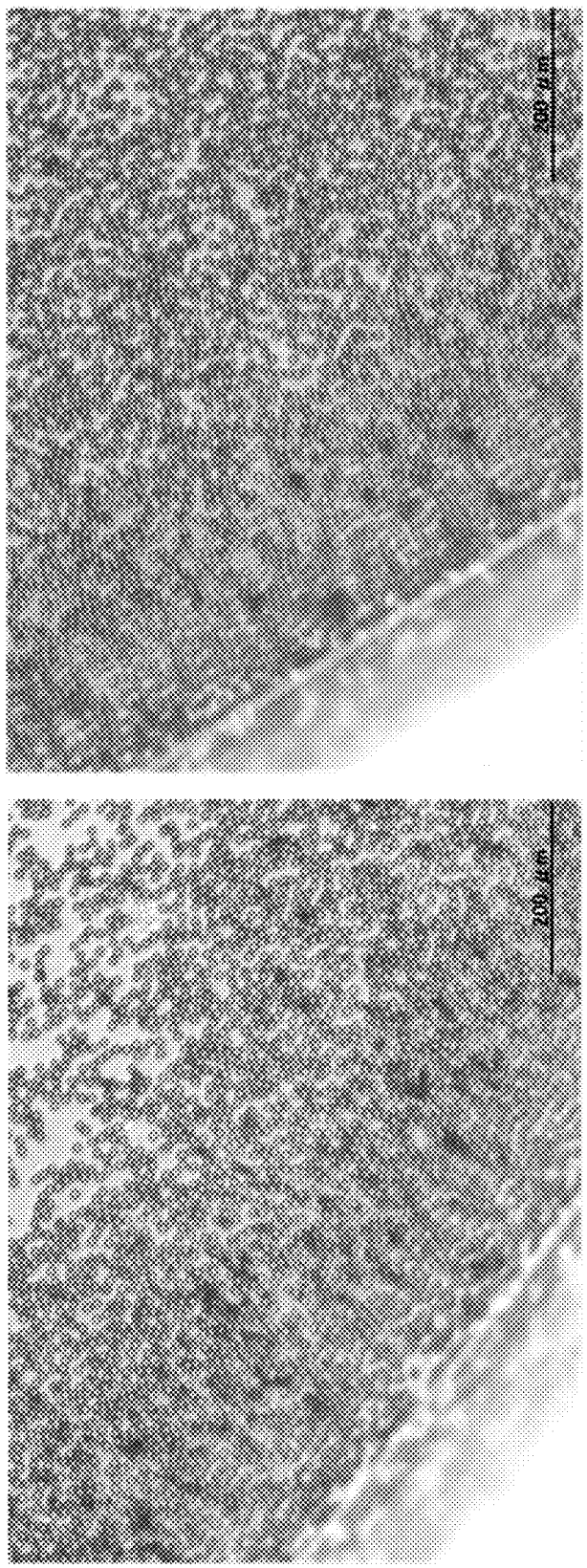

SENSOR CHIP, DETECTION SYSTEM, AND METHOD OF DETECTING TARGET SUBSTANCE IN ANALYTE

CROSS-REFERENCE TO RELATED APPLICATION

This application is based upon and claims the benefit of priority of the prior Japanese Patent application No. 2014-251602, filed on Dec. 12, 2014, the entire contents of which are integrated herein by reference.

STATEMENT REGARDING PRIOR DISCLOSURES BY THE INVENTOR

A document(s) entitled "Fundamental Constitution of On-chip Microbattery for Disposable Immuno-Sensor Chip" and announced at: "The 6th micro-nano mechanics symposium by The Japan Society of Mechanical Engineers" was published on Oct. 13, 2014: by CDROM. The prior disclosures are a document (Whole English) for the presentation, and another document of proceedings. The authors of the publication includes the inventors, Takashiro TSUKAMOTO, Tomohiro ISHIKAWA, and Shuji TANAKA, and a student, Yuto KIMURA, who is not the inventor of this application.

FIELD OF THE INVENTION

The present invention relates to a sensor chip, a detection system, and a method of detecting a target substance in an analyte.

BACKGROUND OF THE INVENTION

Sensor chips for detecting a target substance included in a sample, or an analyte, such as urine or blood, have been well-known. For example, the sensor chip described in Non-Patent Document 1 includes an antenna coil, and energized by electric power supplied by a reader device through the antenna coil through electromagnetic induction.

Non-Patent Document 1: Aytur, T. S. et al., *A 2.2-$mm^2$ CMOS Bioassay Chip and Wireless Interface*, IEEE, 2004 Symposium on VLSI Circuits Digest of Technical Papers, June 2004, pp. 314-317

SUMMARY OF THE INVENTION

In such a configuration, the electric power supplied to a sensor chip declines as the cross-section of the antenna coil decreases. The electric power supplied to sensor chip also reduces as the distance between the sensor chip and a reader device increases.

In the configuration where the sensor chip is disposed in a sample, the sensor chip is generally located distant from the reader device. The sensor chip may not be supplied with sufficient electric, unless an antenna coil with a greater cross-section is provided.

In the meantime, as the planar dimensions (areas) of sensor chips is increased, the cost to manufacture the sensor chip (i.e., manufacturing cost) rises. The sensor chips as described above therefore generally require increased manufacturing costs.

An object of the present invention is to reduce the area of a sensor chip.

In one aspect, a sensor chip is provided, which includes: first and second electrodes that are exposed from the sensor chip and are made from materials different from each other;

a detection circuit that detects a target substance included in an analyte, the detection circuit being driven by a potential difference between the first and second electrodes, the potential difference being generated by an oxidation at the first electrode and a reduction at the second electrode while the analyte contacts the first and second electrodes, the analyte including an electrolyte.

In another aspect, a detection system is provided which includes a sensor chip and an obtainment unit.

The sensor chip includes:

first and second electrodes that are exposed from the sensor chip and are made from materials different from each other;

a detection circuit that detects a target substance included in an analyte, the detection circuit being driven by a potential difference between the first and second electrodes, the potential difference being generated by an oxidation at the first electrode and a reduction at the second electrode while the analyte contacts the first and second electrodes, the analyte including an electrolyte; and an output circuit that outputs a result of the detection by being driven by the potential difference.

The obtainment unit obtains a result of the detection output from the sensor chip.

In a further aspect, a method of detecting a target substance in an analyte is provided, which includes:

contacting first and second electrodes to the analyte including an electrolyte, the first and second electrodes being exposed from a sensor chip and being made from materials different from each other;

generating a potential difference between the first and second electrodes by an oxidation at the first electrode and a reduction at the second electrode; and detecting the target substance included in the analyte by the sensor chip driven by the potential difference.

BRIEF DESCRIPTIONS OF THE DRAWINGS

FIG. 6 is a block diagram illustrating the function of the LSI circuit in FIG. 2;

FIG. 8 illustrates charts illustrating an electrical signal output by the sensor chip in FIG. 1;

FIGS. 16A and 16B are optical microscopic images of ELISA plates in the third experimental example;

DETAILED DESCRIPTION OF THE INVENTION

Hereinafter, embodiments of a sensor chip, an obtainment unit, a detection system, and a method of detecting a target substance in an analyte, of the present invention will be described with reference to FIGS. 1-31.

[First Embodiment]
(Configuration)

Figure 1:
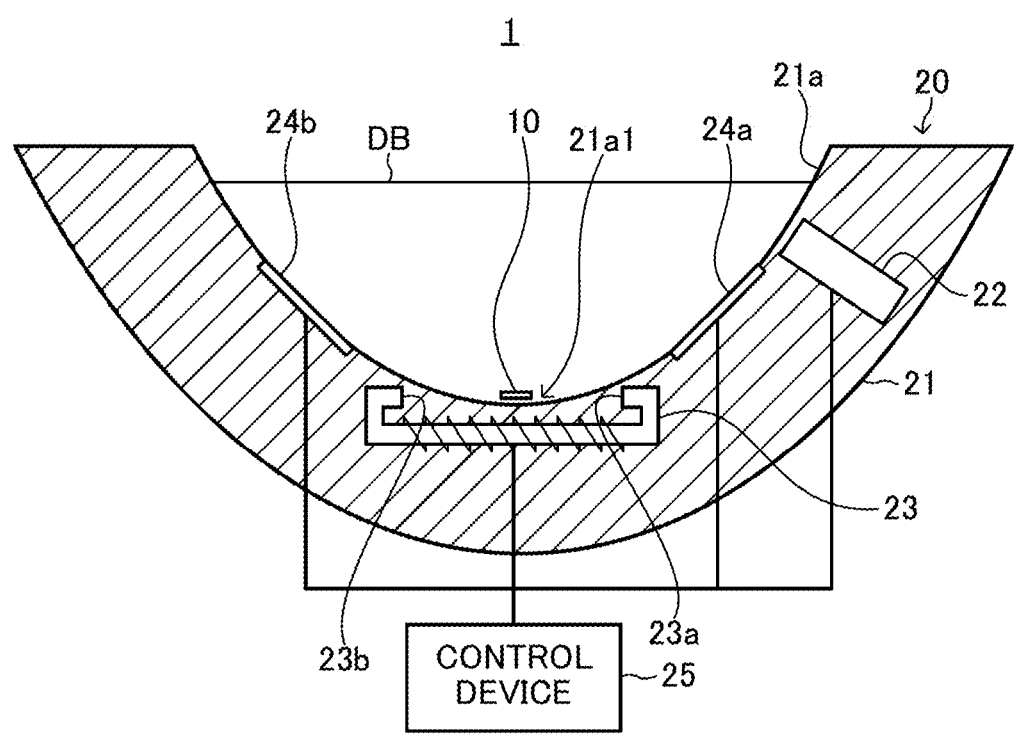
FIG. 1 is a diagram illustrating the configuration of a detection system of a first embodiment.

Referring to FIG. 1, a detection system 1 of a first embodiment includes a sensor chip 10 and an obtainment unit 20. The sensor chip 10 detects a target substance in an analyte (sample) DB and outputs a result of the detection. The obtainment unit 20 obtains, from the sensor chip 10, the result of the detection output by the sensor chip 10.

The analyte DB is a medium (e.g., liquid, solid, colloid, sol, or gel) containing an electrolyte. In the present example, the analyte DB is urine. Alternatively, the analyte DB may be a biological sample (e.g., blood, serum, or blood plasma) other than urine. The analyte DB may be liquids wherein a biological sample is diluted with a buffer solution, such as Phosphate Buffered Saline (PBS).

To the analyte DB, salts, such as sodium chloride (NaCl), ammonium fluoride ($NH_4F$), or zinc chloride ($ZnCl_2$) may be added. Substances for adjusting the potential hydrogen or power of hydrogen (pH) may be added to the analyte DB, such as hydrochloric acid, hydroxide potassium, citric acid, gluconic acid, succinic acid, potassium carbonate, sodium hydrogencarbonate, carbon dioxide, or lactic acid.

Figure 2:
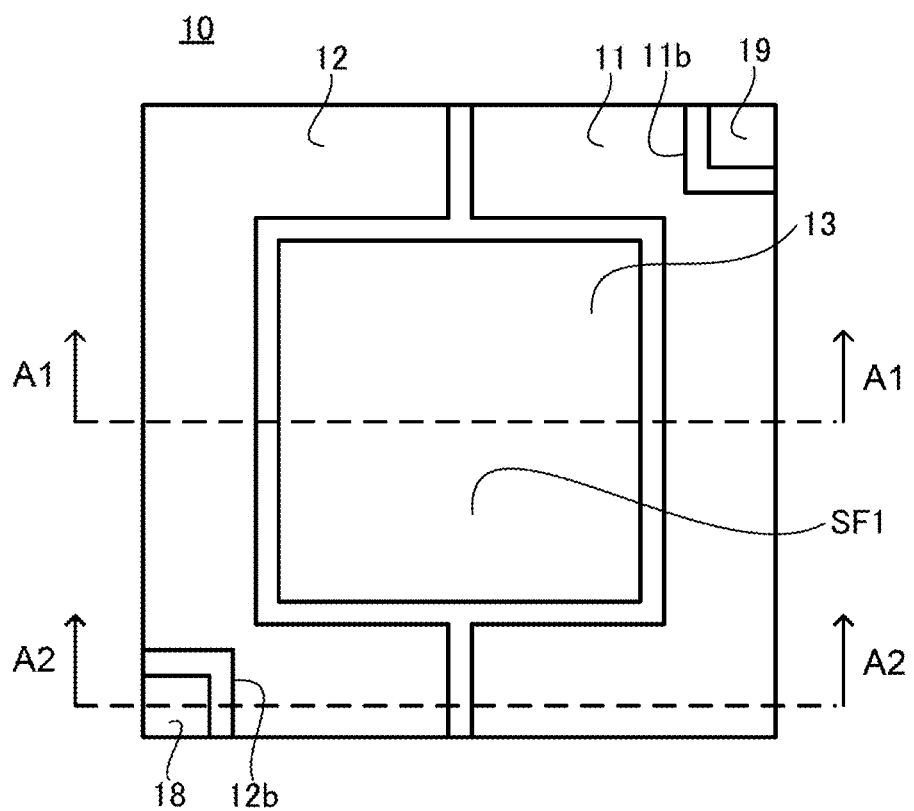
FIG. 2 is a front view illustrating the configuration of the sensor chip in FIG. 1.

The sensor chip 10 is a planer-shaped semiconductor device having a pair of surfaces which are parallel to each other. As shown in FIG. 2, the sensor chip 10 has a square shape, when viewed in the thickness direction of the sensor chip 10 (i.e., in the front view).

In the present example, in the front view, each side of the sensor chip 10 has a length of 2 mm. Alternatively, each side of the sensor chip 10 may have any length between 10 μm and 10 mm, in the front view. Alternatively, the sensor chip 10 may also have a shape other than a square (e.g., a rectangular, polygonal, oval, or circular shape) in the front view.

Figure 3:
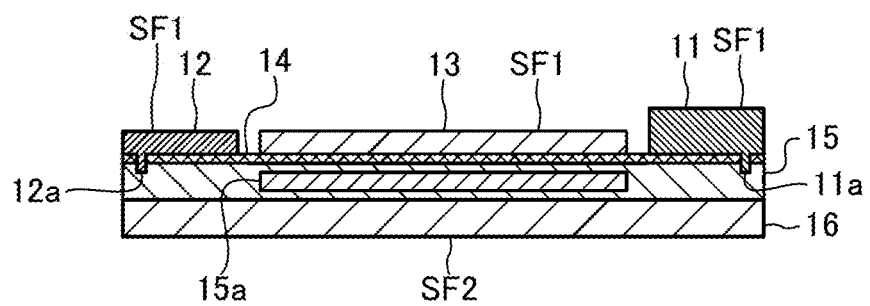
FIG. 3 is a cross-sectional view taken along Line A1-A1 in FIG. 2.
Figure 4:
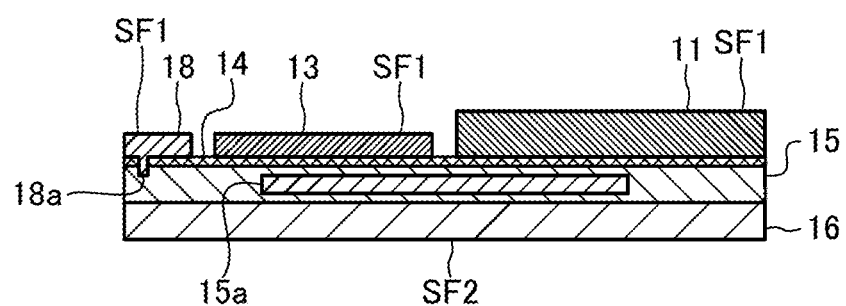
FIG. 4 is a cross-sectional view taken along Line A2-A2 in FIG. 2.

Referring to FIGS. 3 and 4, which are cross-sectional views taken along Lines A1-A1 and A2-A2, in FIG. 2, respectively, the sensor chip 10 includes a first electrode 11, a second electrode 12, an attachment 13, an insulator 14, a large scale integration (LSI) circuit 15, a substrate 16, a third electrode 18, and a fourth electrode 19.

The substrate 16 is made from silicon (Si). The substrate 16 forms a second surface SF2 of a pair of surfaces of the sensor chip 10.

The LSI circuit 15 stacks on the substrate 16, at the surface opposite to the second surface SF2 relative to the substrate 16. The LSI circuit 15 will be described later.

The insulator 14 is made from silicon dioxide ($SiO_2$). The insulator 14 may be referred to as an oxidized silicon film. The insulator 14 stacks on the LSI circuit 15 at the surface opposite to the substrate 16 relative to the LSI circuit 15.

The first electrode 11 is made from zinc (Zn). Alternatively, the first electrode 11 may be made from a metal different from zinc, such as magnesium (Mg). The second electrode 12 is made from platinum (Pt). Alternatively, the second electrode 12 may be made from a metal-based material that is different from the first electrode 11 and is also different from platinum, such as metals including gold (Au), iron (Fe), copper (Cu); or silver chloride (AgCl). The attachment 13 is made from gold (Au). Alternatively, the attachment 13 may be made from a material different from gold.

Alternatively, the second electrode 12 may be made from carbon (C) or a carbon-based material, such as graphite, boron-doped diamond, and carbon nanotubes.

The third electrode 18 is made from platinum (Pt). The third electrode 18 may be made from a metal-based material that is different from platinum, such as metals including gold (Au), iron (Fe), copper (Cu); or silver chloride (AgCl). The fourth electrode 19 is made from platinum (Pt). Alternatively, the fourth electrode 19 may be made from a metal-based material that is different from platinum, such as metals including gold (Au), iron (Fe), copper (Cu); or silver chloride (AgCl). In the present example, the fourth electrode 19 is made from the same metal as the metal of the third electrode 18. Alternatively, the fourth electrode 19 may be made from a metal different from the metal of the third electrode 18. Alternatively, the third electrode 18 and the fourth electrode 19 may be covered with an insulation film.

The first electrode 11, the second electrode 12, the attachment 13, the third electrode 18, and the fourth electrode 19 stack on the insulator 14, at the surface opposite to the LSI circuit 15 relative to the insulator 14. Thereby, a first surface SF1 of the pair of surfaces of the sensor chip 10 is formed by the first electrode 11, the second electrode 12, the attachment 13, the third electrode 18, and the fourth electrode 19. In other words, the first electrode 11, the second electrode 12, the attachment 13, the third electrode 18, and the fourth electrode 19 are exposed from the sensor chip 10 at the first surface SF1.

Now referring to FIG. 2, in the front view of the sensor chip 10, the attachment 13 has a square shape, of which sides are shorter than the sides of the sensor chip 10. In the front view of the sensor chip 10, the centroid of the attachment 13 coincides with the centroid of the sensor chip 10. Alternatively, the attachment 13 may have a shape other than a square (e.g., a rectangular, polygonal, oval, or circular shape), in the front view of the sensor chip 10. The centroid of the attachment 13 may be located anywhere, away from the centroid of the sensor chip 10, in the front view of the sensor chip 10.

In the front view of the sensor chip 10, the first electrode 11 and the second electrode 12 are positioned closer to the periphery of the sensor chip 10 than the attachment 13. In the front view of the sensor chip 10, the first electrode 11 and the second electrode 12 have the respective predetermined widths, and each have a U-shape along the periphery of the sensor chip 10.

The second electrode 12 has a notch 12b at a first corner of the sensor chip 10, in the front view of the sensor chip 10. The first electrode 11 has a notch 11b at a second corner of the sensor chip 10, in the front view of the sensor chip 10. The second corner is located at the opposite angle to the first corner. The first electrode 11 and the second electrode 12 have the same shape, in the front view of the sensor chip 10.

In the front view of the sensor chip 10, both the third electrode 18 and the fourth electrode 19 have a square shape, of which sides are shorter than the sides of the first electrode 11 and the second electrode 12. The third electrode 18 is positioned at the first corner of the sensor chip 10, in the front view of the sensor chip 10. The fourth electrode 19 is positioned at the second corner of the sensor chip 10, in the front view of the sensor chip 10.

Alternatively, in the front view of the sensor chip 10, both the third electrode 18 and the fourth electrode 19 may have shapes (e.g., rectangular, polygonal, oval, or circular shapes) other than a square.

In the front view of the sensor chip 10, the first electrode 11, the second electrode 12, the attachment 13, the third electrode 18, and the fourth electrode 19 are spaced apart at a certain distance.

Alternatively, the first electrode 11 and the second electrode 12 may have shapes different from each other, in the front view of the sensor chip 10. The first electrode 11 and the second electrode 12 may also have planar dimensions (areas) different from each other, in the front view of the sensor chip 10.

Referring to FIG. 3, the first electrode 11 is thicker than the second electrode 12. The first electrode 11 may have a thickness between 50 nm and 10 μm, for example. The second electrode 12 may have a thickness between 20 nm and 50 μm, for example. Alternatively, the first electrode 11 and the second electrode 12 may have the same thickness.

As shown in to FIG. 3, the second electrode 12 and the attachment 13 have the same thickness. Alternatively, the second electrode 12 and the attachment 13 may have different thicknesses.

Referring to FIG. 4, the second electrode 12 and the third electrode 18 have the same thickness. Alternatively, the second electrode 12 and the third electrode 18 may have different thicknesses. In this case, the third electrode 18 and the fourth electrode 19 have the same thickness.

Figure 5:
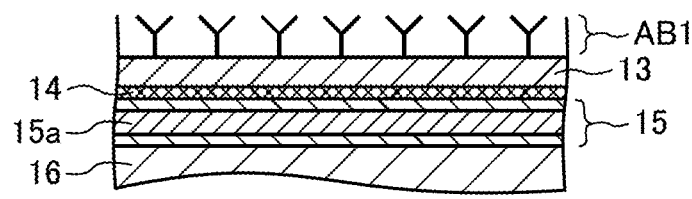
FIG. 5 is an enlarged view of the attachment in FIG. 3.

Referring to FIG. 5, a plurality of chip-side antibodies AB1 are attached to the surface of the surfaces of the attachment 13, opposite to the insulator 14 (i.e., the part of the first surface SF1, which is formed from the attachment 13). The chip-side antibodies AB1 have affinity with (i.e., are capable of binding to) antigens which is the target substance. In the present example, the chip-side antibodies AB1 are mono-clonal antibodies. Alternatively, the chip-side antibodies AB1 may be poly-clonal antibodies. The chip-side antibodies AB1 are an example of first antibody.

The antigens are insulin, casein, immunoglobulin E (IgE), immunoglobulin G (IgG), and infectious substances, such as bacterium or viruses, for example.

Referring back to FIG. 3, the first electrode 11 includes a connector 11a passing through the insulator 14. The connector 11a connects the first electrode 11 to the LSI circuit 15. The second electrode 12 includes a connector 12a passing through the insulator 14. The connector 12a connects the second electrode 12 to the LSI circuit 15.

Referring back to FIG. 4, the third electrode 18 includes a connector 18a passing through the insulator 14. The connector 18a connects the third electrode 18 to the LSI circuit 15. In the present example, similarly to the third electrode 18, the fourth electrode 19 includes a connector that passes through the insulator 14 for connecting the fourth electrode 19 to the LSI circuit 15.

While the analyte DB contacts the first electrode 11 and the second electrode 12, oxidation occurs at the first electrode 11 as expressed in the following chemical reaction (1), whereas reduction occurs at the second electrode 12 as expressed in the following chemical formulae (2) and (3). The term "while the analyte DB contacts the first electrode 11 and the second electrode 12" refer to the situation where the sensor chip 10 is disposed (e.g., immersed) into the analyte DB, for example.

$$Zn \rightarrow Zn^{2+} + 2e^- \quad (1)$$

$$O_2 + 2H^+ + 2e^- \rightarrow H_2O_2 \quad (2)$$

$$2H^+ + H_2O_2 + 2e^- \rightarrow 2H_2O \quad (3)$$

While the analyte DB contacts the first electrode 11 and the second electrode 12, a potential difference (i.e., voltage) is generated between the first electrode 11 and the second electrode 12 caused by the oxidation at the first electrode 11 and the reduction at the second electrode 12. The LSI circuit 15 is driven by this potential difference generated between the first electrode 11 and the second electrode 12.

The oxidation at the first electrode 11 causes the first electrode 11 to elute into the analyte DB. Therefore, the total available electric power generated by the first electrode 11 and the second electrode 12 increases as the volume of the first electrode 11 increases (the area and thickness of the first electrode 11 increase).

Now, the LSI circuit 15 will be described. Referring to FIG. 6, the LSI circuit 15 includes a magnetic sensor 15a, an analog-to-digital converter (ADC) 15c, a modulator 15d, and an amplifier 15e. The magnetic sensor 15a represents an example of a detection circuit. The ADC 15c, the modulator 15d, and the amplifier 15e collectively represent an example of an output circuit.

Referring back to FIG. 3, the magnetic sensor 15a is positioned so as to correspond to the location of the attachment 13, in the front view of the sensor chip 10. The magnetic sensor 15a detects magnetic field in the thickness direction of the sensor chip 10 at positions corresponding to the respective chip-side antibodies AB1, thereby counting how many antigens bind to chip-side antibodies AB1, and then generating a signal indicative of the detected antigen count. In the present example, the magnetic sensor 15a includes a plurality of Hall elements.

How the magnetic sensor 15a detects antigens will be described.

Figure 7A:
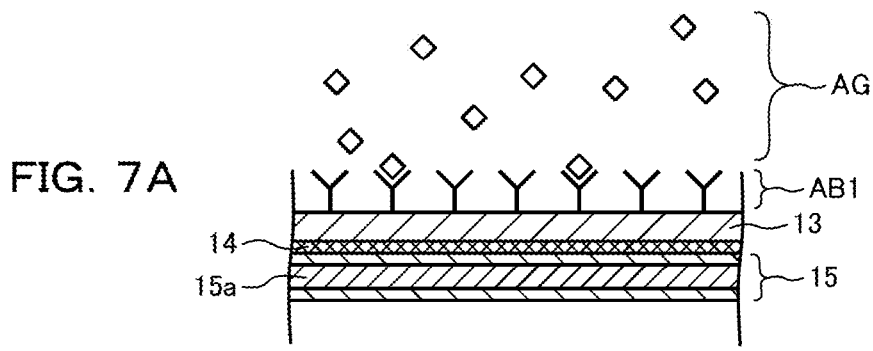
FIGS. 7A-7D are schematic diagrams illustrating how antigens are detected by the sensor chip in FIG. 1.
Figure 7B:
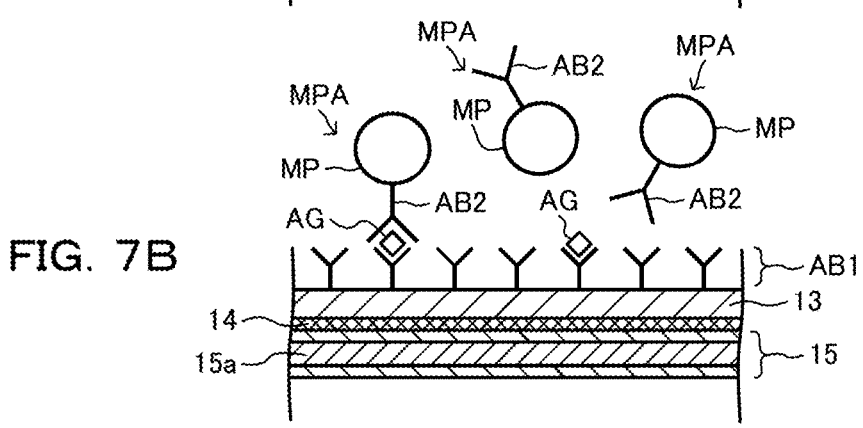
Figure 7C:
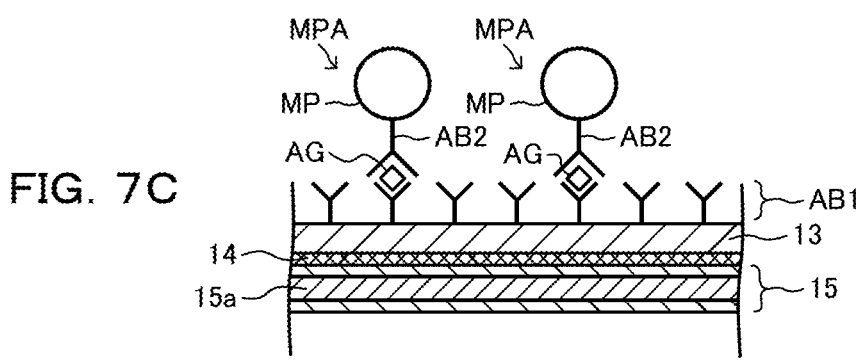

Referring to FIG. 7C, some antigens AG bind to both chip-side antibodies AB1 and particle-side antibodies AB2. In the present example, the particle-side antibodies AB2 are mono-clonal antibodies. Alternatively, the particle-side antibodies AB2 may be poly-clonal antibodies. The particle-side antibodies AB2 represent an example of second antibody.

The particle-side antibodies AB2 have magnetized particles MP attached thereto. The magnetized particles MP are also known as magnetic beads. The magnetized particles MP have diameters between 10 nm and 10 µm, for example. In the present example, the magnetized particles MP having the particle-side antibodies AB2 attached thereto are also referred to as antibody-attached magnetized particles MPA.

The antibody-attached magnetized particles MPA are attached to the attachment 13, having the antigens AG and the chip-side antibodies AB1 interposed therebetween.

Figure 7D:
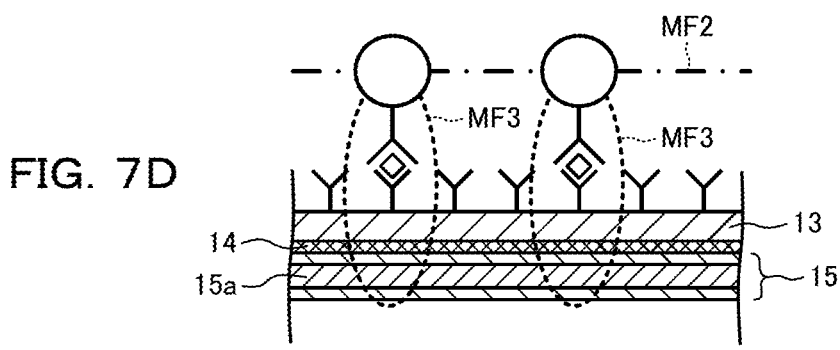
Figure 9:
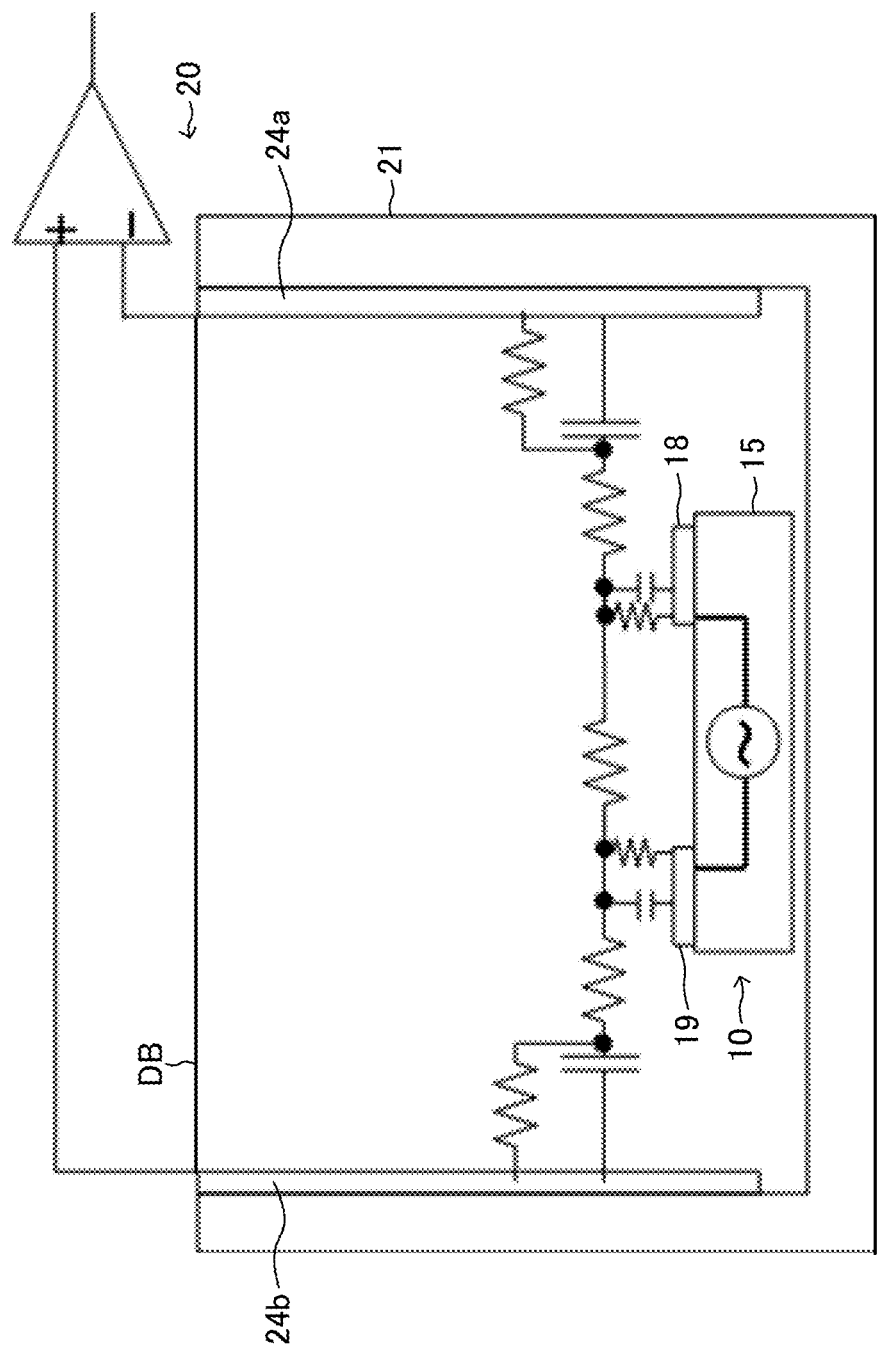
FIG. 9 is a schematic diagram illustrating an electric circuit equivalent to an electric circuit constructed in the detection system in FIG. 1.

In this example, magnetic field MF2 parallel to the sensor chip 10 is generated, as shown in FIG. 7D. In this case, when the antibody-attached magnetized particles MPA are attached to the attachment 13, the magnetized particles MP of the antibody-attached magnetized particles MPA generate magnetic fields MF3 in the thickness direction of the sensor chip 10, in the vicinity of the magnetized particles MP. As described later, the magnetic field MF2 is generated by the obtainment unit 20.

In this manner, the magnetic sensor 15a counts how many antigens bind to chip-side antibodies AB1, by detecting the magnetic fields MF3 in the thickness direction of the sensor chip 10. Accordingly, it can be regarded that the magnetic sensor 15a detects magnetized particles MP that are bound to chip-side antibodies AB1, having particle-side antibodies AB2 and antigens AG interposed therebetween.

The ADC 15c shown in FIG. 6 converts the signal generated by the magnetic sensor 15a, from the analog format into a digital signal.

The modulator 15d modulates the signal converted by the ADC 15c, in accordance with a predetermined modulation scheme. In the present example, the modulation scheme is the Frequency Shift Keying (FSK). In the present example, as shown in Chart (A) in FIG. 8, a modulated signal has a first frequency representing a value of "1", in the durations T1 and T3; and a second frequency lower than the first frequency, representing a value of "0", in the duration T2. Alternatively, the second frequency may be higher than the first frequency.

Alternatively, the modulation scheme may be a scheme different from the FSK, such as the Phase Shift Keying (PSK) or the Amplitude Shift Keying (ASK).

The amplifier 15e amplifies the signal modulated by the modulator 15d, and outputs the amplified signal out of the sensor chip 10 via the third electrode 18 and the fourth electrode 19. How electrical signals output via the third electrode 18 and the fourth electrode 19 are conducted will be described later.

In the present example, the distance between the third electrode 18 and the fourth electrode 19 is greater than the distance between the first electrode 11 and the second electrode 12. Thus, it is assured that electrical signals output from the sensor chip 10 are made closely correlated to electrical signals detected by the obtainment unit 20.

Alternatively, in the LSI circuit 15, the amplifier 15e may amplify a signal that has been converted by the ADC 15c and has not been modulated. In such a configuration, the LSI circuit 15 includes no modulator 15d. In this configuration, as shown in Chart (B) in FIG. 8, the amplified signal has a first voltage representing a value of "1", in the durations T1 and T3, and a second voltage lower than the first voltage, representing a value of "0", in the duration T2. Alternatively, the second voltage may be higher than the first voltage.

Referring back to FIG. 1, the obtainment unit 20 includes a cell 21, a first magnet 22, a second magnet 23, a fifth electrode 24a, a sixth electrode 24b, and a control device 25. The cell 21, the fifth electrode 24a and the sixth electrode 24b collectively form a container. The control device 25 represents an example of a detector.

The cell 21 is configured so as to contain, in the volume formed by an inner wall 21a of the cell 21, the analyte DB, and the sensor chip 10 located in the analyte DB. In the present example, the vertical-direction bottom (i.e., the lowest portion) 21a1 of the inner wall 21 is parallel to the horizontal direction.

The first magnet 22 is positioned slightly below the top of the inner wall 21a. The obtainment unit 20 includes a driving mechanism (not shown), and the driving mechanism moves the first magnet 22 between the position near the inner wall 21a and the position spaced apart from the inner wall 21a at a certain distance.

When the first magnet 22 is in the position near the inner wall 21a, the first magnet 22 attracts at least one magnetized particle MP (if present) in the analyte DB, which does not bind to a chip-side antibody AB1, toward the first magnet 22, as described later.

Alternatively, in place of the driving mechanism, the obtainment unit 20 may include a shield mechanism, and the shield mechanism may switch the obtainment unit 20 between a mode to shield the magnetic field generated by the first magnet 22 and another mode not to shield the magnetic field.

In the present example, the first magnet 22 is a permanent magnet. Alternatively, the first magnet 22 may be an electromagnet. In the latter configuration, the obtainment unit 20 includes no driving mechanism.

The second magnet 23 is located in the vicinity of the bottom 21a1 of the inner wall 21a. The line connecting between a pair of magnetic poles 23a and 23b of the second magnet 23 is parallel to the bottom 21a1 of the inner wall 21a (in the present example, coincides with the horizontal direction). When disposed, the sensor chip 10 is often positioned to be parallel to the bottom 21a1 of the inner wall 21a. Accordingly, the line connecting between the pair of magnetic poles 23a and 23b of the second magnet 23 can be said as being parallel to the sensor chip 10.

As described above, the second magnet 23 is configured to generate the magnetic field MF2 that is parallel to the bottom 21a1 of the inner wall 21a, in the vicinity of the bottom 21a1 of the inner wall 21a.

In the present example, the second magnet 23 is an electromagnet. In the present example, the second magnet 23 generates an alternating current magnetic field. Alternatively, the second magnet 23 may generate a direct current magnetic field.

The fifth electrode 24a and the sixth electrode 24b are exposed at the surface of the inner wall 21a in the volume defined by the inner wall 21a, when the cell 21 is empty (i.e., contains no analyte DB). The fifth electrode 24a and the sixth electrode 24b are located in the vicinity of the bottom 21a1 of the inner wall 21a. This ensures that the fifth electrode 24*a* and the sixth electrode 24*b* contact an analyte DB when the cell 21 contains the analyte DB.

The analyte DB includes an electrolyte. Thus, the third electrode 18 and the fourth electrode 19 are regarded as being electrically connected to the fifth electrode 24*a* and the sixth electrode 24*b* through the analyte DB. For example, the electric circuit constructed by the sensor chip 10, the obtainment unit 20, and the analyte DB is regarded as being equivalent to an electric circuit shown in FIG. 9.

Thus, an electrical signal output from the LSI circuit 15 via the third electrode 18 and the fourth electrode 19 is conducted to the obtainment unit 20 through the analyte DB, in the form of a potential difference between the fifth electrode 24*a* and the sixth electrode 24*b*.

The control device 25 shown in FIG. 1 detects the potential difference between the fifth electrode 24*a* and the sixth electrode 24*b*. The control device 25 obtains the result as to whether antigens AG are detected in the analyte DB, from the sensor chip 10 based on the detected potential difference.

In the present example, the control device 25 stores the obtained result of the detection into a storage device (not shown). Alternatively, the control device 25 may output the obtained result of the detection through an output device (e.g., a display or a speaker). The control device 25 may also send the obtained result of the detection to an external device that is connected through a communication network.

(Operations)

Next, the operations of the detection system 1 will be described.

Figure 10A:
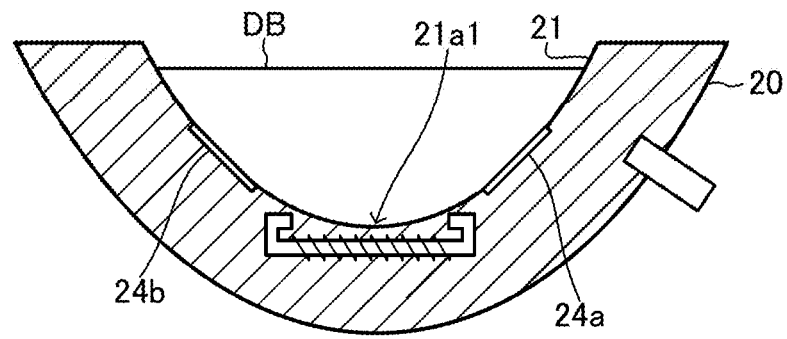
FIGS. 10A-10D are schematic diagrams illustrating an operation of the detection system in FIG. 1.

Referring to FIG. 10A, an analyte DB is disposed into the cell 21 of the obtainment unit 20. This causes the fifth electrode 24*a* and the sixth electrode 24*b* to contact the analyte DB.

Figure 10B:
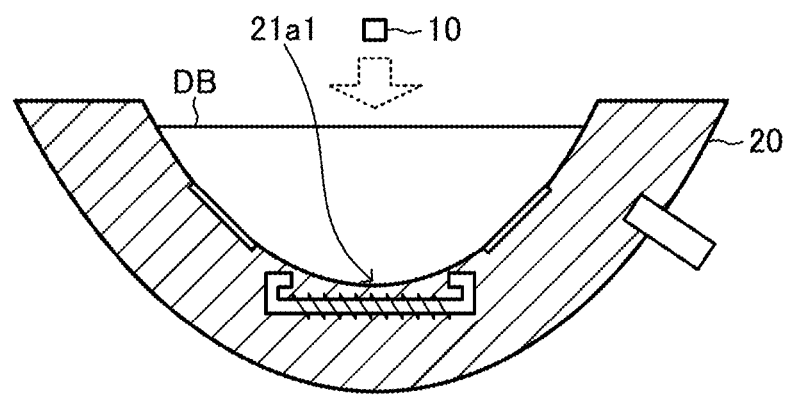

Then, as shown in FIG. 10B, the sensor chip 10 is disposed into the analyte DB. This causes the first electrode 11, the second electrode 12, the third electrode 18, and the fourth electrode 19 to contact the analyte DB. The sensor chip 10 falls down the analyte DB, toward the bottom 21*a*1 of the cell 21.

When the sensor chip 10 is disposed into the analyte DB, as shown in FIG. 7A, a part of the antigens AG in the analyte DB bind to chip-side antibodies AB1. Oxidation occurs at the first electrode 11 whereas reduction occurs at the second electrode 12, which results in generation of a potential difference between the first electrode 11 and the second electrode 12 once the sensor chip 10 is disposed into the analyte DB. The potential difference drives the LSI circuit 15. The oxidation at the first electrode 11 also causes elution of the first electrode 11 into the analyte DB.

Figure 10C:
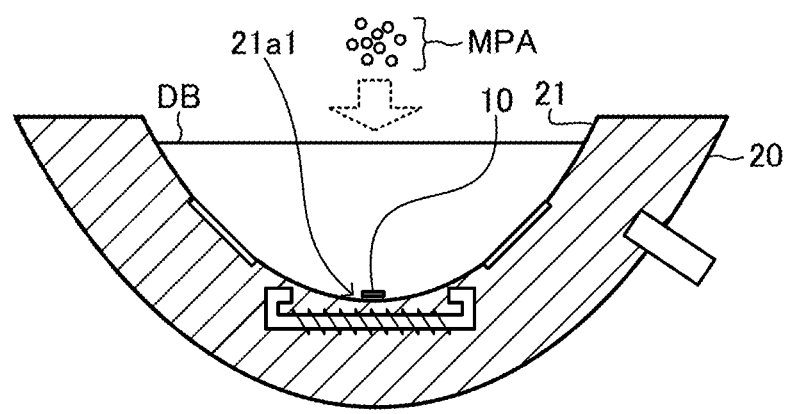

Then, as shown in FIG. 10C, the sensor chip 10 reaches the bottom 21*a*1 of the cell 21, and is positioned so as to be parallel to the bottom 21*a*1 of the cell 21.

After a predetermined duration, a plurality of antibody-attached magnetized particles MPA are added to the analyte DB. Alternatively, the plurality of antibody-attached magnetized particles MPA may be added to the analyte DB, together with a buffer solution (e.g., PBS).

Figure 10D:
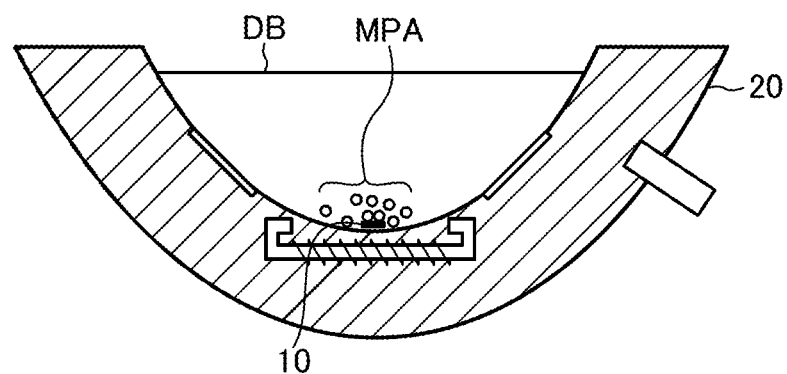

The plurality of antibody-attached magnetized particles MPA then fall down the analyte DB toward the bottom 21*a*1 of the cell 21. When the antibody-attached magnetized particles MPA come closer to the sensor chip 10, at least part of particle-side antibodies AB2 of the antibody-attached magnetized particles MPA bind to antigens AG that have been bound to the chip-side antibodies AB1, as shown in FIGS. 7B and 10D. As a result, those magnetized particles MP are attached to the attachment 13, having the particle-side antibodies AB2, antigens AG, and the chip-side antibodies AB1 interposed therebetween.

Figure 11A:
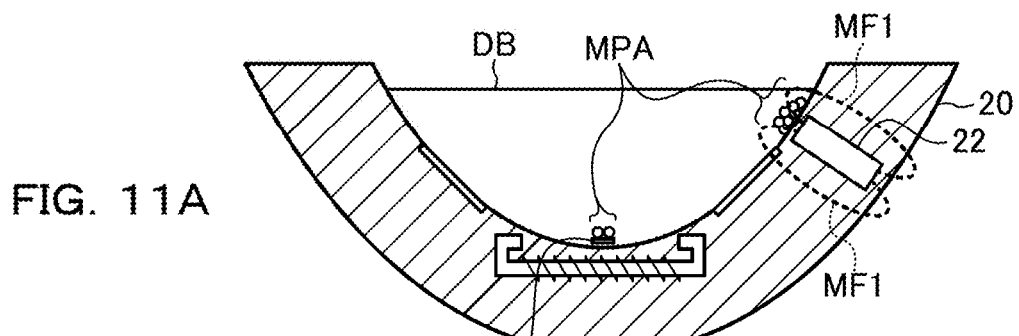
FIGS. 11A-11D are schematic diagrams illustrating the operation of the detection system in FIG. 1.

After a predetermined duration, as shown in FIG. 11A, the obtainment unit 20 moves the first magnet 22, from the position spaced apart from the inner wall 21*a* at the certain distance, to the position near the inner wall 21*a*. This results in a magnetic field MF1 generated in the analyte DB.

In the magnetic field MF1, the first magnet 22 attracts antibody-attached magnetized particles MPA that have not been attached to the attachment 13, in the analyte DB (i.e., magnetized particles MPA that are not bound to antigens AG binding to chip-side antibodies AB1), toward the first magnet 22. As a result, as shown in FIG. 7C, the antibody-attached magnetized particles MPA that have not been attached to the attachment 13 are removed from the vicinity of the sensor chip 10.

Figure 11B:
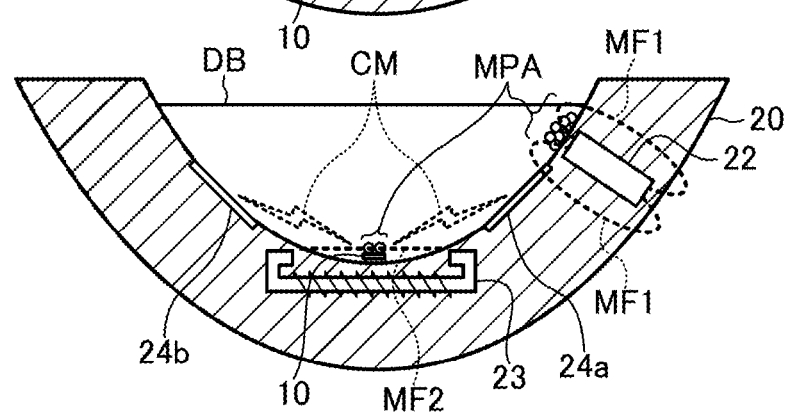

As shown in FIG. 11B, the obtainment unit 20 then energizes the second magnet 23 to generate a magnetic field MF2 parallel to the sensor chip 10. As a result, as shown in FIG. 7D, magnetic fields MF3 in the thickness direction of the sensor chip 10 are generated near the positions where the antibody-attached magnetized particles MPA are attached.

Using the LSI circuit 15 driven by the potential difference generated between the first electrode 11 and the second electrode 12, the sensor chip 10 detects the magnetic fields MF3 in the thickness direction of the sensor chip 10, to count how many antigens AG have bound to chip-side antibodies AB1.

Then, using the LSI circuit 15 driven by the potential difference generated between the first electrode 11 and the second electrode 12, the sensor chip 10 outputs an electrical signal indicative of the detected count of antigens AG, via the third electrode 18 and the fourth electrode 19.

The electrical signal CM output from the sensor chip 10 via the third electrode 18 and the fourth electrode 19 is conducted to the obtainment unit 20 through the analyte DB, as a deviation in the potential difference between the fifth electrode 24*a* and the sixth electrode 24*b*.

Figure 11C:
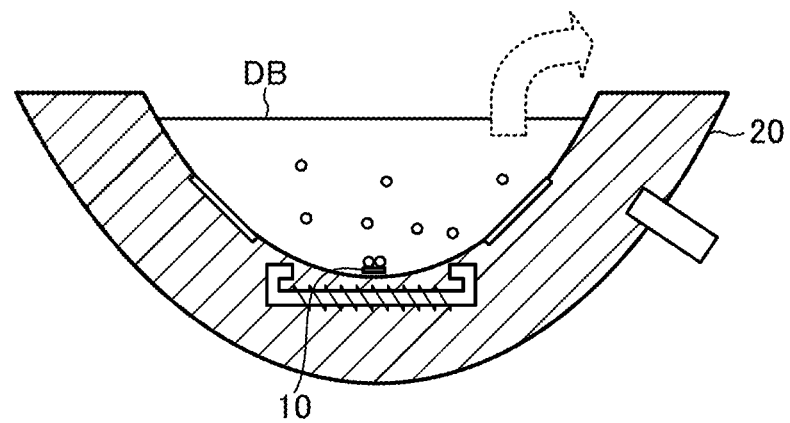

Then, as shown in FIG. 11C, the obtainment unit 20 moves the first magnet 22, from the position near the inner wall 21*a*, to the position spaced apart from the inner wall 21*a* at the certain distance. This causes the magnetic field MF1 generated in the analyte DB to be eliminated. The obtainment unit 20 also stop energizing the second magnet 23. The magnetic field MF2 generated in the analyte DB is also eliminated.

Thereafter, the analyte DB, the sensor chip 10, and the antibody-attached magnetized particles MPA are drained from the cell 21. The obtainment unit 20 may include a filter for catching at least one of the sensor chip 10, and the antibody-attached magnetized particles MPA drained from the cell 21.

Figure 11D:
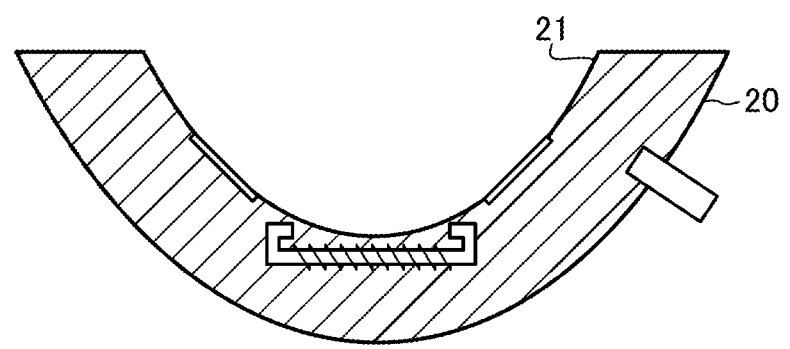

Then, as shown in FIG. 11D, the cell 21 of the obtainment unit 20 is emptied out, without containing any analyte DB. At this timing, the obtainment unit 20 may clean the inner wall 21*a* of the cell 21.

FIRST EXPERIMENTAL EXAMPLE

Next, a first experimental example of the present invention will be described.

In the first experimental example, respective cyclic voltammograms were measured for zinc and platinum.

As a working electrode, a circular electrode with a diameter of 3 mm was used. As a counter electrode, a circular electrode was used, which had a diameter of 10 mm and was made from platinum. A silver/silver chloride (Ag/AgCl)

reference electrode was used as a reference electrode. PBS (available from Wako Pure Chemical Industries, Ltd., Osaka, Japan) was used as an electrolyte solution. The applied voltage was swept at a speed of 20 mV/s.

Figure 12:
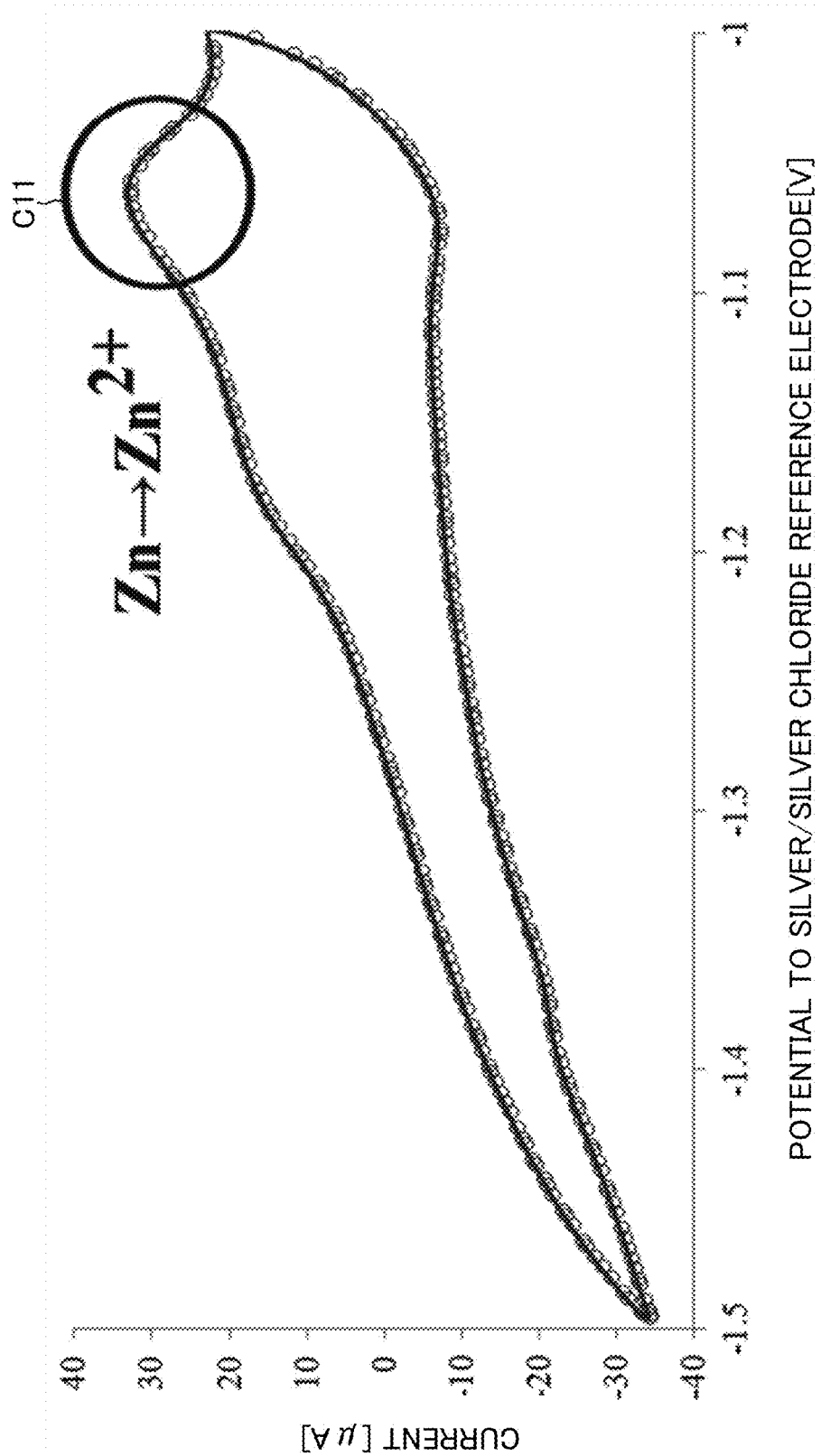
FIG. 12 is a cyclic voltammogram for zinc in a first experimental example.

FIG. 12 shows a cyclic voltammogram when a zinc electrode was used as the working electrode. It is considered that the peak at Region C11 in FIG. 12 corresponded to the above chemical reaction (1).

Figure 13:
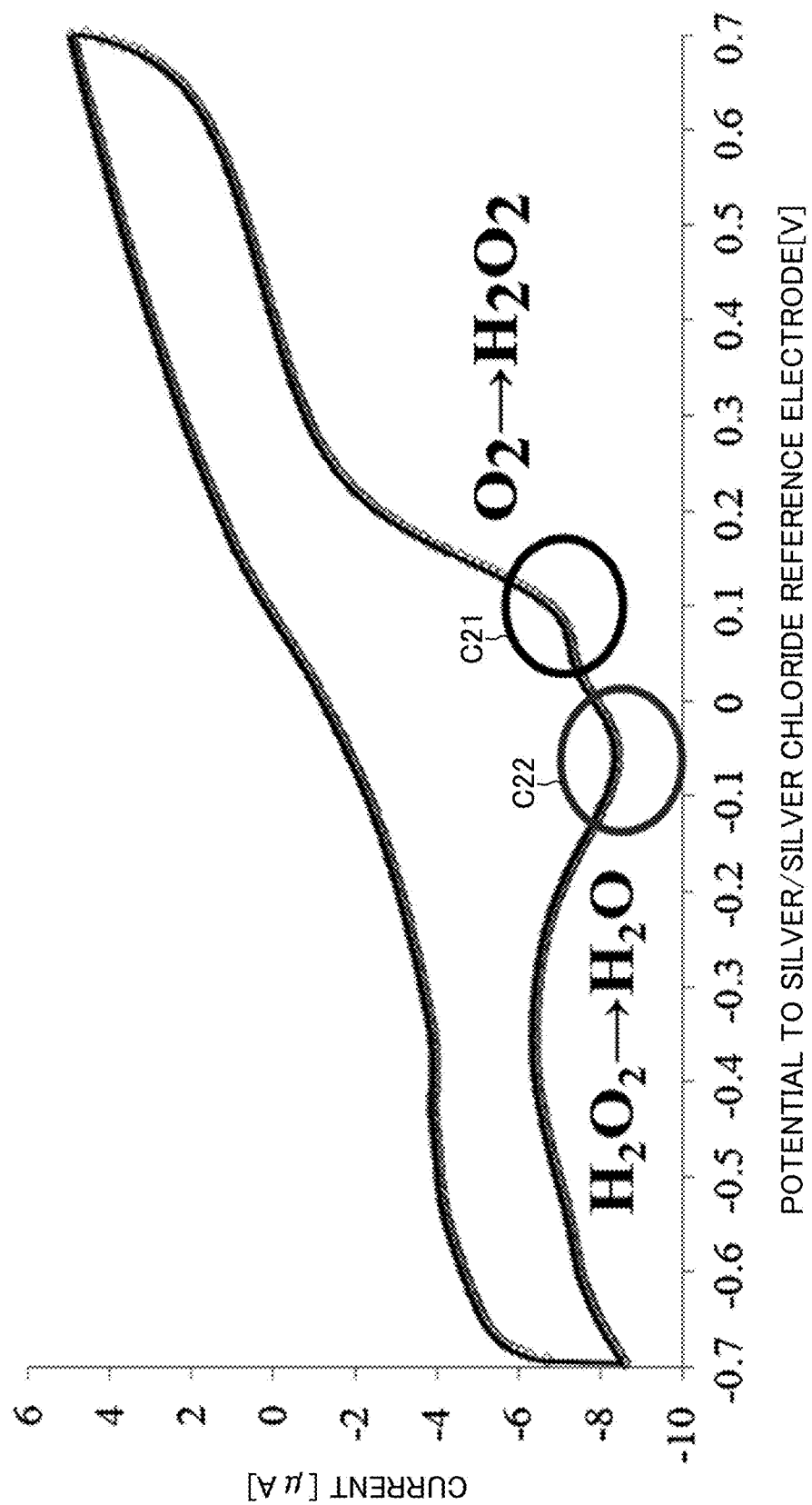
FIG. 13 is a cyclic voltammogram for platinum in the first experimental example.

FIG. 13 shows a cyclic voltammogram when a platinum electrode was used as the working electrode. It is considered that the peak at Region C21 in FIG. 13 corresponded to the above chemical reaction (2), whereas the peak at Region C22 in FIG. 13 are regarded as corresponding to the above chemical reaction (3).

SECOND EXPERIMENTAL EXAMPLE

Next, a second experimental example of the present invention will be described.

The second experimental example studied electric power generation using both a zinc electrode and a platinum electrode.

A first circular electrode that had a diameter of 3 mm and was made from zinc, and a second circular electrode that had a diameter of 3 mm and was made from platinum, were immersed into an electrolyte solution, such that these electrodes faced against from each other, with a distance of 10 mm defined therebetween. As the electrolyte solution, 50 mL of PBS was used.

Figure 14:
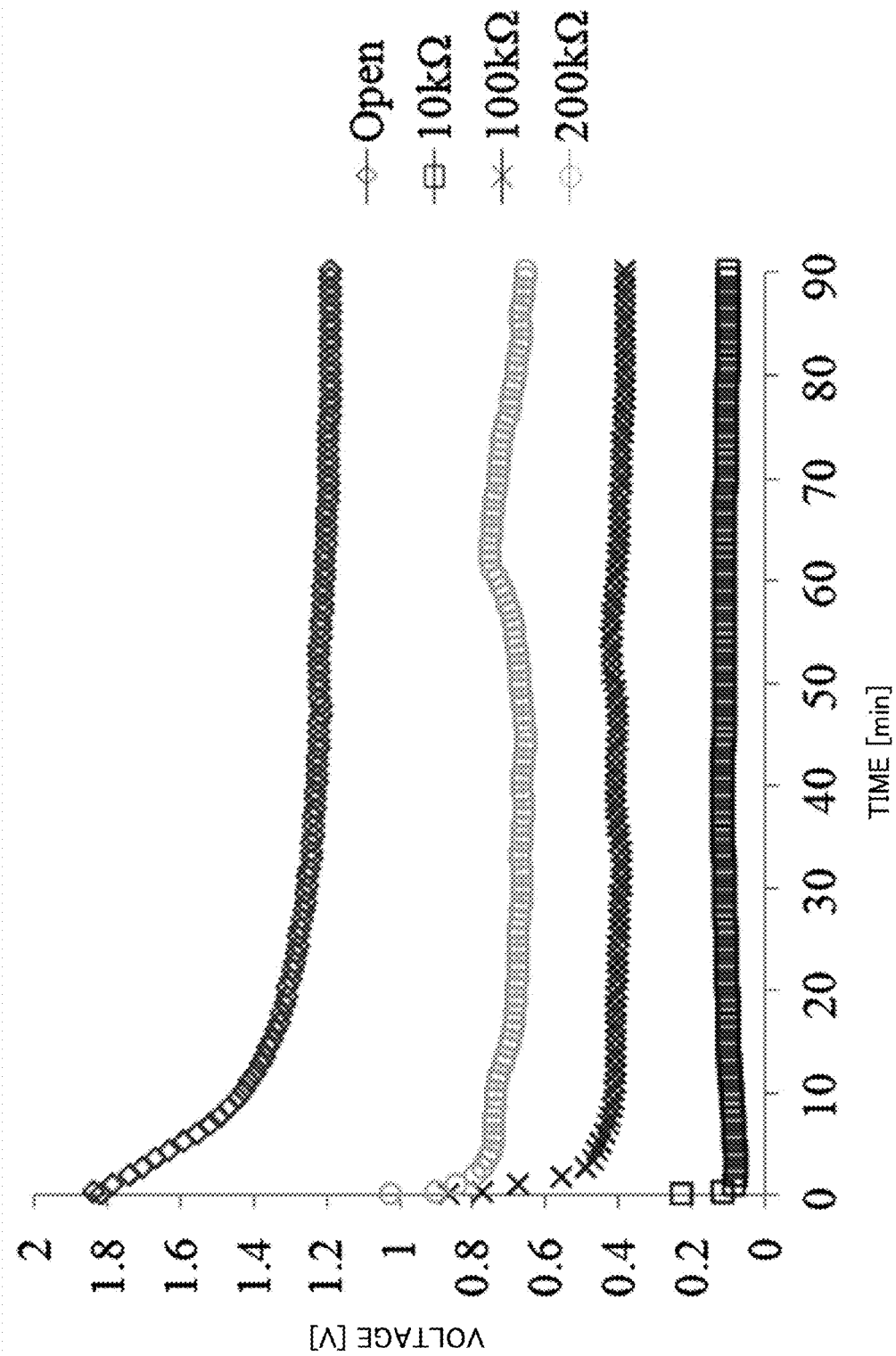
FIG. 14 is a chart illustrating changes in potential differences generated between electrodes over time when external resistances were varied, in a second experimental example.

FIG. 14 shows a change in the potential difference (i.e., voltage) generated between the electrodes over time when external resistances were varied. The external resistances were: an open circuit (i.e., Open), 10 k$\Omega$, 100 k$\Omega$, and 200 k$\Omega$.

When the first and second electrodes constructed an open circuit, the potential difference generated between the electrodes in the steady state was about 1.2 V. It is considered that both the chemical reactions (2) and (3) described above occurred at the second electrode.

From the change in the potential difference generated between the electrodes when the external resistances were varied, the internal resistance was estimated to be about 200 k$\Omega$. This internal resistance in the second experimental example was relatively high. It was considered that this relatively high internal resistance was caused by a reduction in the potential difference due to a leakage current and a formation of a diffusion layer. The leakage current is a current flowing between the first and second electrodes through the electrolyte solution. The formation of a diffusion layer is the phenomenon where the above chemical reaction (1) is inhibited by an increased zinc ion level near the first electrode.

As shown in FIG. 14, the potential differences generated between the electrodes were the highest immediately after the electrodes were immersed in the electrolyte solution. At this point, the maximum electric power available using the first and second electrodes was about 5.3 $\mu$W. The average of the maximum electric power available using the first and second electrodes in the steady state was about 2.4 $\mu$W. The second experimental example demonstrated that the first and second electrodes can generate a stable electric power for 90 minutes.

THIRD EXPERIMENTAL EXAMPLE

Next, a third experimental example of the present invention will be described.

The third experimental example studied the effects of elution of the zinc electrode on the antigen-antibody binding.

To a first ELISA (Enzyme-Linked ImmunoSorbent Assay) plate and a second ELISA plate, first antibodies in 100 $\mu$L of PBS were added dropwise. Goat anti-human IgG-FC was used as the first antibodies. Per 1 mL of PBS, 10 $\mu$g of the first antibodies were added. As a result, the first antibodies were attached to the first and second ELISA plates.

Then, only to the first ELISA plate, the first antibodies in 100 $\mu$L of PBS were added dropwise. Human IgG was used as antigens. Per 1 mL of PBS, 20 $\mu$g of the first antibodies were added. As a result, antigens were caused to bind to the first antibodies on the first ELISA plate.

Then, to the first and second ELISA plates, the antibody-attached magnetized particles in 100 $\mu$L of PBS were added dropwise. The antibody-attached magnetized particles contained goat anti-human IgG-H+L, as second antibodies. The magnetized particles of the antibody-attached magnetized particles had diameters of 2.8 $\mu$m. Per 1 mL of PBS, 1 g of the antibody-attached magnetized particles were added. Per 1 mg magnetized particles, 1 mg of the second antibodies were added. As a result, on the first ELISA plate, the first antibodies were bound to the antigens, which in turn were bounded to the second antibodies, and the antibody-attached magnetized particles were attached to the first ELISA plate.

Then, the first and second ELISA plates were washed for removing any free antibody-attached magnetized particles.

Figure 15B:
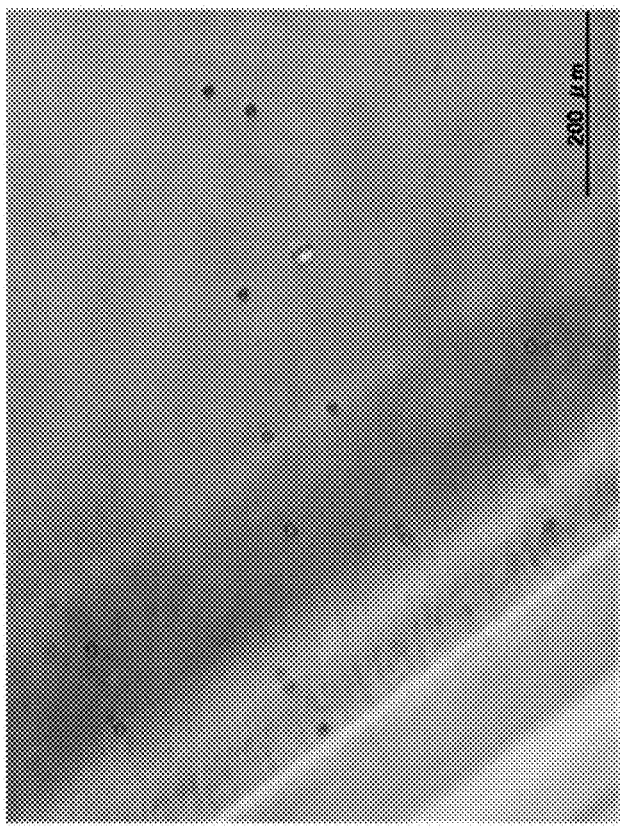
FIGS. 15A and 15B are optical microscopic images of ELISA plates in a third experimental example.
Figure 15A:
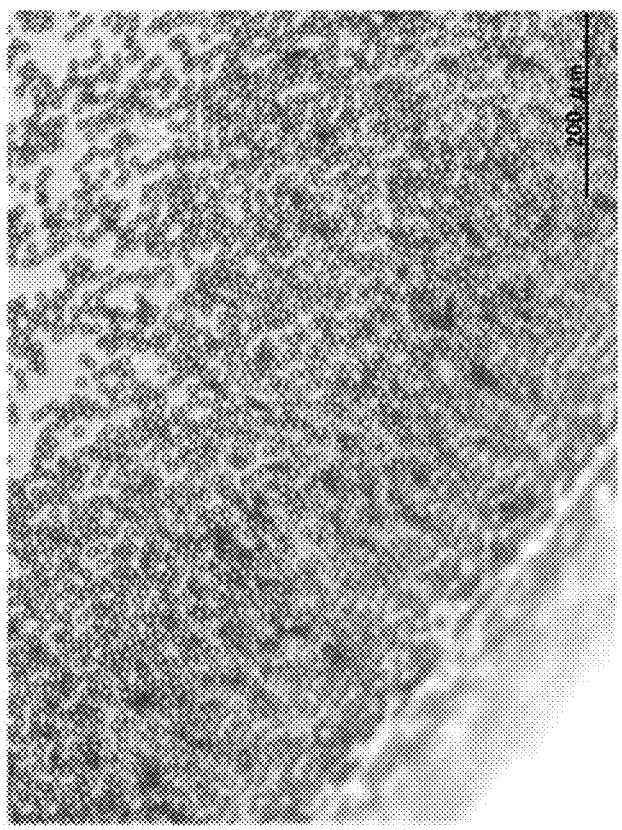

FIG. 15A is an optical microscopic image of the first ELISA plate. FIG. 15B is an optical microscopic image of the second ELISA plate. As shown in FIGS. 15A and 15B, significantly larger number of magnetized particles were attached to the first ELISA plate than the second ELISA plate. Thus, the third experimental example demonstrated that the antigen-antibody binding assisted attachment of the magnetized particles to the first ELISA plate.

To the first ELISA plate having the magnetized particles attached thereto, 340 $\mu$L of PBS were added dropwise as an electrolyte solution. Then, a first circular electrode that had a diameter of 3 mm and was made from zinc and a second circular electrode that had a diameter of 3 mm and was made from platinum were immersed into the electrolyte solution. The first and second electrodes are connected to an external resistance of 200 k$\Omega$. The electrolyte solution was stirred at every five minutes.

FIG. 16A is an optical microscopic image of the first ELISA plate before the first and second electrodes were immersed into the electrolyte solution. FIG. 16B is an optical microscopic image of the first ELISA plate, after 30 minutes after the first and second electrodes were immersed into the electrolyte solution. As shown in FIGS. 16A and 16B, there was no significant difference in the densities of the magnetized particles.

No magnetized particles detached from the first ELISA plate were observed when the electrolyte solution was stirred. It is demonstrated that the antigen-antibody binding was maintained after the first and second electrodes were immersed into the electrolyte solution.

The potential difference generated between the electrodes in the steady state was about 1.0 V. The average of the maximum electric power available using the first and second electrodes in the steady state was about 4.9 $\mu$W.

The zinc ion level after 30 minutes after the first and second electrodes were immersed into the electrolyte solution was estimated to be about 119 $\mu$mol, based on the electric power output from the first and second electrodes.

Accordingly, it is demonstrated that zinc ions of about 119 µmol had an only small effect on the antigen-antibody binding.

It is expected that the sensor chip 10 can operate for several to dozens of minutes in the detection system 1. The detection system 1 is expected to have the same zinc ion level as that in the third experimental. This means that the target substance contained in an analyte DB can be detected quite precisely, in the detection system 1.

FOURTH EXPERIMENTAL EXAMPLE

Next, a fourth experimental example of the present invention will be described.

The fourth experimental example studied conduction of electrical signals through the analyte DB.

Figure 17:
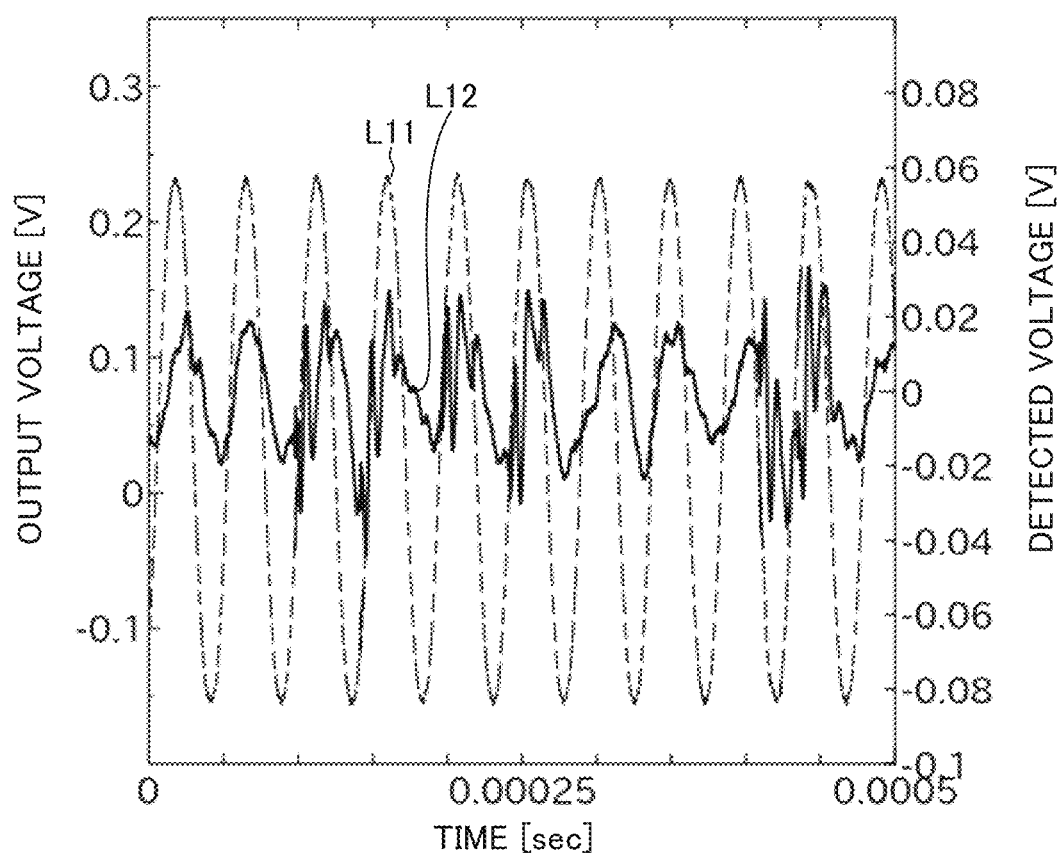
FIG. 17 is a chart illustrating changes in the output and detected voltages over time, in a fourth experimental example.

FIG. 17 shows changes in output and detected voltages over time. The output voltage is the voltage representing electrical signals output via the third electrode 18 and the fourth electrode 19. The detected voltage refer to the voltage detected as the potential difference between the fifth electrode 24a and the sixth electrode 24b. In FIG. 17, Curve L11 indicates the output voltage, whereas Curve L12 indicates the detected voltage.

As shown in FIG. 17, the detected voltage was highly correlated with the output voltage. This means that the result of the detection by the sensor chip 10 is conducted to the obtainment unit 20 in a reliable manner, in the detection system 1.

Figure 18:
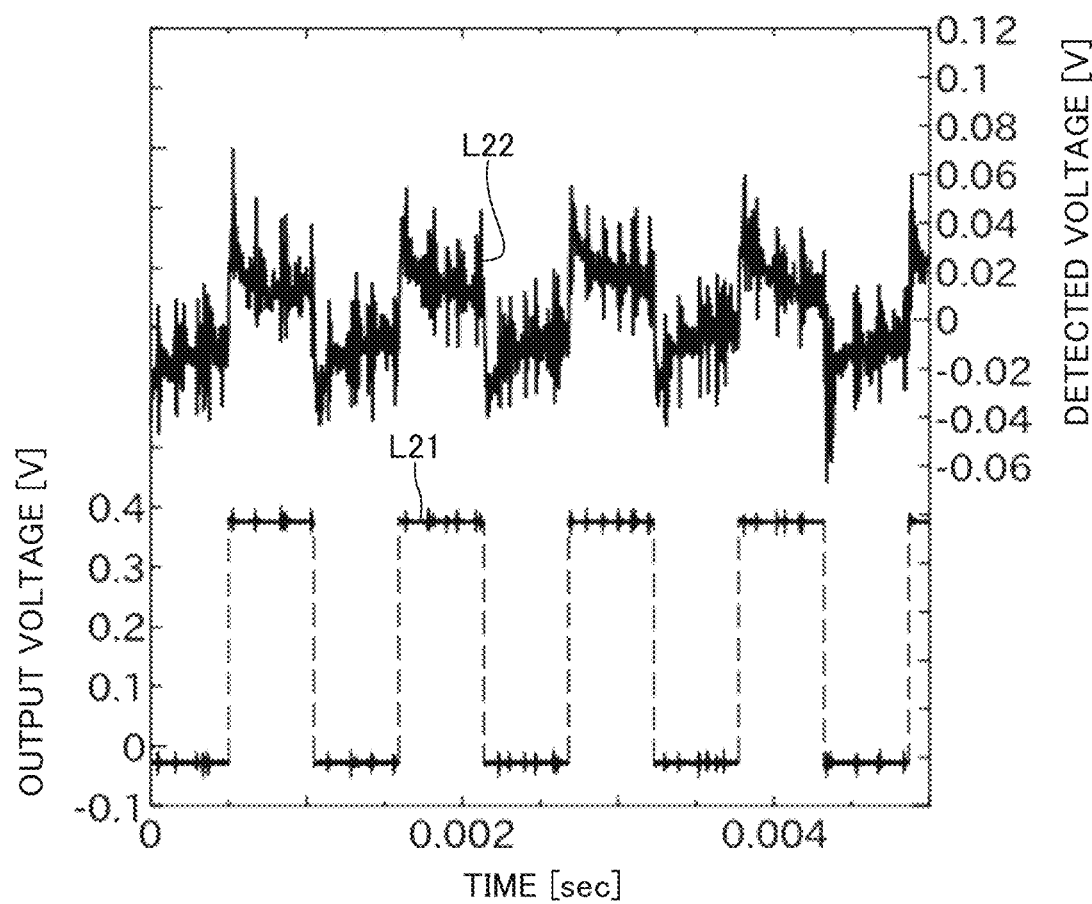
FIG. 18 is a chart illustrating changes in the output and detected voltages over time, in the fourth experimental example.

FIG. 18 shows changes in the output and detected voltages over time, when no modulation was made in the LSI circuit 15. In FIG. 18, Curve L21 indicates the output voltage, whereas Curve L22 indicates the detected voltage. Again, as shown in FIG. 18, detected voltage was highly correlated with the output voltage. This means that the result of the detection by the sensor chip 10 is conducted to the obtainment unit 20 in a reliable manner, in the detection system 1.

As described above, the sensor chip 10 of the first embodiment includes the first electrode 11 and the second electrode 12 that are exposed from the sensor chip 10 and are made from metals different from each other. The sensor chip 10 further includes the magnetic sensor 15a that detects a target substance included in the analyte DB, the magnetic sensor 15a being driven by a potential difference between the first electrode 11 and the second electrode 12, the potential difference being generated by an oxidation at the first electrode 11 and a reduction at the second electrode 12 while the analyte DB contacts the first electrode 11 and the second electrode 12, the analyte DB including an electrolyte.

In accordance with this configuration, the magnetic sensor 15a is driven without requiring any antenna coil. The planar dimension of the sensor chip 10 hence can be reduced, as compared to that of a sensor chip having an antenna coil.

Furthermore, the sensor chip 10 of the first embodiment further includes chip-side antibodies AB1 having an affinity for antigens AG that is the target substance. The sensor chip 10 further includes the magnetic sensor 15a that detects at least one of magnetized particles MP including second antibodies AB2 having an affinity for the antigens AG bound to the first antibodies AB1, having the second antibodies AB2 and the antigens AG interposed therebetween.

Before filing the present application, the magnitudes of the effects of the elution of the electrode into the analyte DB on antigen-antibody binding and the accuracy of detection of magnetized particles, were not clear. The present inventor demonstrated that such effects are minor. Thus, the target substance can be detected quite precisely, in the detection system 1.

Furthermore, the sensor chip 10 of the first embodiment further includes the LSI circuit 15 that outputs a result of the detection by being driven by the potential difference generated between the first electrode 11 and the second electrode 12.

In accordance with this configuration, the magnetic sensor 15a is driven without requiring any antenna coil. The planar dimension of the sensor chip 10 hence can be reduced, as compared to that of a sensor chip having an antenna coil.

Furthermore, in the sensor chip 10 of the first embodiment, the LSI circuit 15 outputs, via the third electrode 18 and the fourth electrode 19, an electrical signal indicative of the result of the detection.

In accordance with this configuration, without requiring any antenna coil, the electrical signal indicative of the result of the detection can be conducted to the obtainment unit 20 external to the sensor chip 10, through the analyte DB. The planar dimension of the sensor chip 10 hence can be reduced, as compared to that of a sensor chip having an antenna coil.

Furthermore, the sensor chip 10 of the first embodiment has a planer shape having a pair of surfaces which are parallel to each other. Additionally, the first electrode 11 and the second electrode 12 are exposed from the sensor chip 10 at the first surface SF1 of the pair of surfaces.

In accordance with this configuration, the first electrode 11 and the second electrode 12 can be formed, in a single step for processing a single surface. Accordingly, the sensor chip 10 can be manufactured more readily, as compared to a structure where the first electrode 11 is formed on the first surface SF1 and the second electrode 12 is formed on the second surface SF2.

Furthermore, in the sensor chip 10 of the first embodiment, the first electrode 11 is made from zinc.

Zinc is ubiquitously found in living bodies. The analyte DB containing commonly-present zinc thus would not significantly modify the properties of the analyte DB. Hence, in accordance with the sensor chip 10, any elution of the first electrode 11 into the analyte DB would have a limited effect on the accuracy of detection of the target substance. As a result, the target substance can be detected with a sufficiently high accuracy.

A first electrode 11 made from magnesium also has the similar advantageous effects as those of the first electrode 11 made from zinc.

When the target substance is infectious substance and a sample is urine, for example, it is preferred that a sensor chip can be disposed after a single use (i.e., disposable sensor chip). In accordance with the sensor chip 10 of the first embodiment, since the planar dimension of the sensor chip 10 is sufficiently reduced, the manufacturing cost for the sensor chip 10 can be reduced. The sensor chip 10 hence can be preferably used as a disposable sensor chip.

In the first embodiment, the chip-side antibodies AB1 are attached to the attachment 13. Alternatively, the sensor chip 10 may not include an attachment 13. In the latter configuration, the chip-side antibodies AB1 are attached to the insulator 14.

Furthermore, in the first embodiment, the sensor chip 10 is an immunity sensor (i.e., immuno sensor) that detects the target substance, based on the antigen-antibody binding. Alternatively, the sensor chip 10 may be a bio sensor other than the immunity sensor, such as an enzyme sensor, a microorganism sensor, or an ion channel sensor. In such a configuration, the target substance may be glucose, or lactic acid, or the like.

Figure 19:
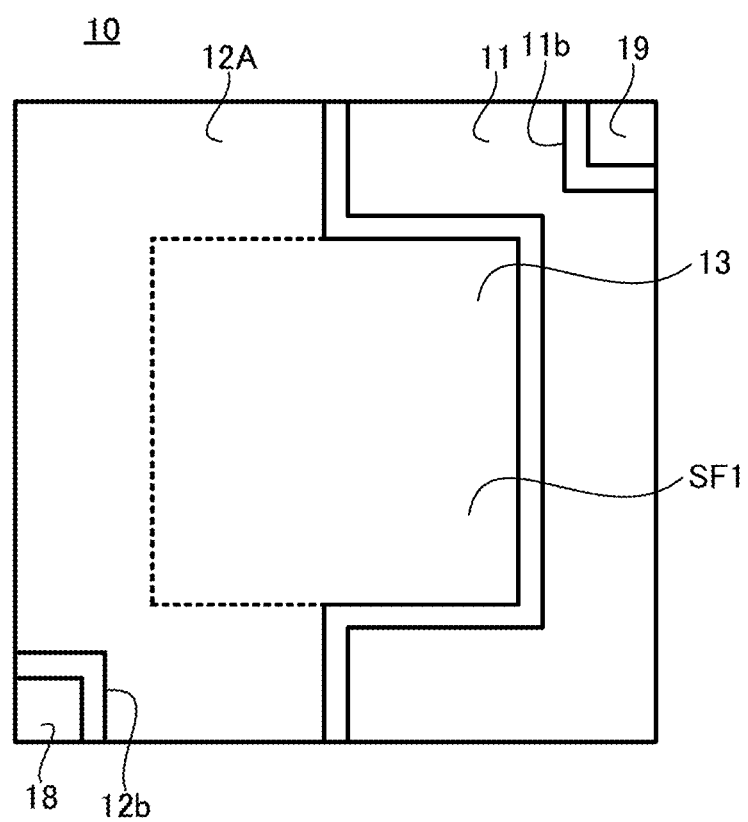
FIG. 19 is a front view illustrating the configuration of a modification to the sensor chip in FIG. 1.

Alternatively, as shown in FIG. 19, in place of the second electrode 12, the sensor chip 10 may include a second electrode 12A. The second electrode 12A is formed integrally with the attachment 13. Reduction hence occurs both at the second electrode 12A and at the attachment 13. In accordance with this configuration, the substantial planar dimension of the second electrode 12A can be reduced.

Figure 20:
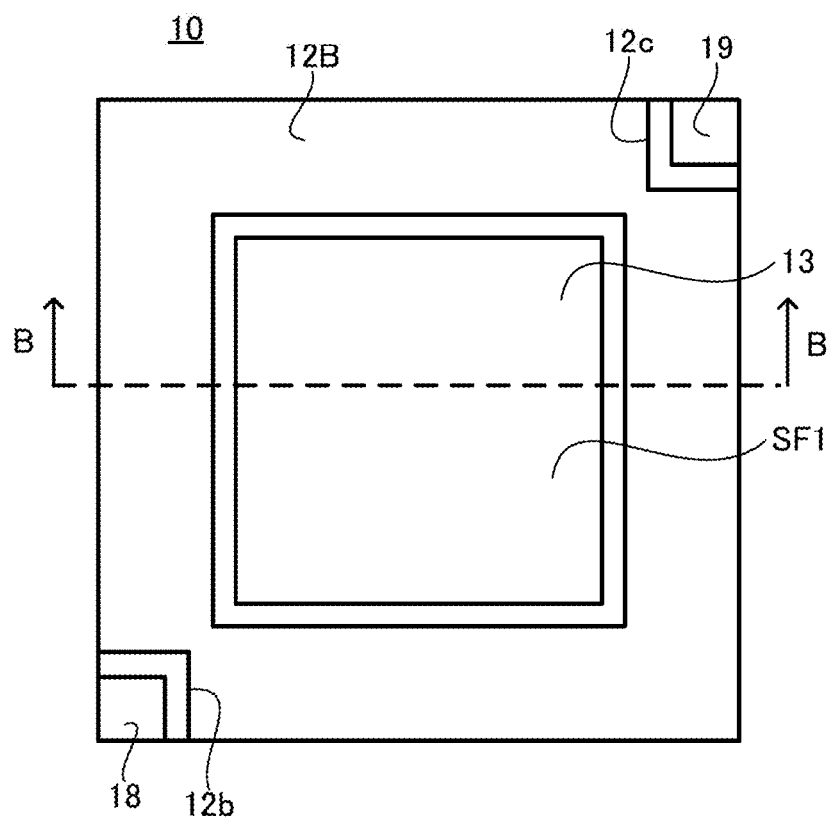
FIG. 20 is a front view illustrating the configuration of another modification to the sensor chip in FIG. 1.
Figure 21:
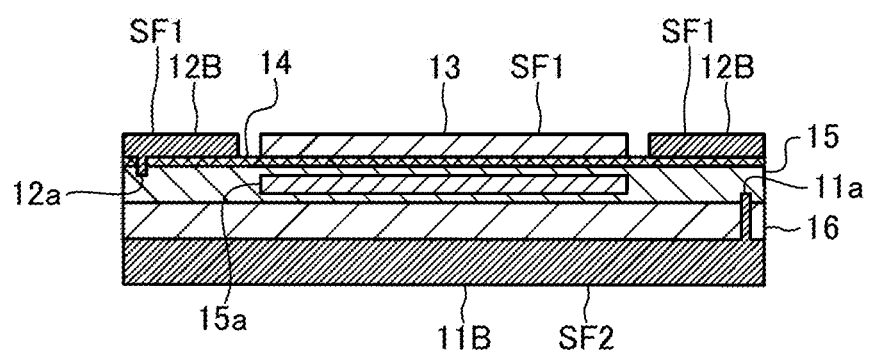
FIG. 21 is a cross-sectional view taken along Line B-B in FIG. 20.

Furthermore, as shown in FIG. 20, and FIG. 21 that is a cross-sectional view taken along Line B-B in FIG. 20, in place of the first electrode 11 and the second electrode 12, the sensor chip 10 may include a first electrode 11B and a second electrode 12B, respectively.

Referring to FIG. 21, the first electrode 11B stacks on the substrate 16, at the surface opposite to the LSI circuit 15 relative to the substrate 16. The first electrode 11B has the same shape as that of the sensor chip 10, in the front view of the sensor chip 10. In this manner, the first electrode 11B forms the second surface SF2 of the pair of surfaces of the sensor chip 10. In other words, the first electrode 11B is exposed from the sensor chip 10 at the second surface SF2.

Referring to FIG. 20, the second electrode 12B surrounds the attachment 13 such that the second electrode 12B is located at closer to the periphery of the sensor chip 10 than the attachment 13, in the front view of the sensor chip 10. In other words, the second electrode 12B has a predetermined width and is formed around the periphery of the sensor chip 10, in the front view of the sensor chip 10.

The second electrode 12B includes a notch 12b at the first corner of the sensor chip 10, and a notch 12c at the second corner of the sensor chip 10, in the front view of the sensor chip 10.

In the front view of the sensor chip 10, the second electrode 12B, the attachment 13, the third electrode 18, and the fourth electrode 19 are spaced apart at a certain distance. The second electrode 12B forms the first surface SF1 of the pair of surfaces of the sensor chip 10. In other words, the second electrode 12B are exposed from the sensor chip 10 at the first surface SF1.

In accordance with this configuration, the planar dimensions of the electrodes 11B and 12B can be increased, as compared to the configuration where both the first electrode 11 and the second electrode 12 are formed on a single surface. The wider electrodes 11B and 12B contribute to reduce the impedances of the reactions at the electrodes. As a result, the potential difference between the first electrode 11B and the second electrode 12B is prevented from declining. The planar dimension of the sensor chip 10 can also be reduced.

Figure 22:
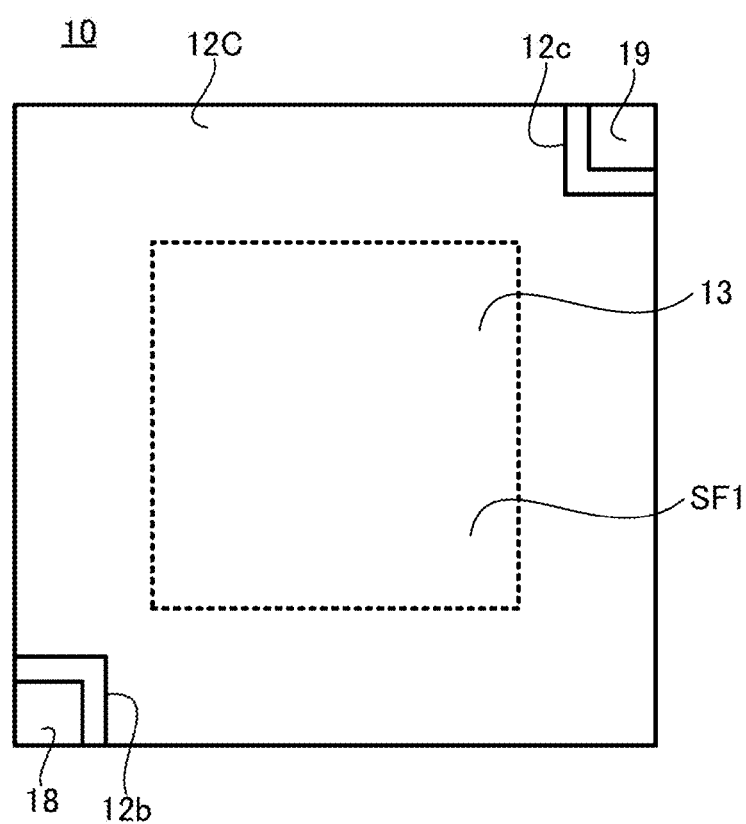
FIG. 22 is a front view illustrating the configuration of another modification to the sensor chip in FIG. 1.

In this configuration, as shown in FIG. 22, in place of the second electrode 12B, the sensor chip 10 may include a second electrode 12C. The second electrode 12C is formed integrally (monolithically) with the attachment 13. Reduction occurs both at the second electrode 12C and at the attachment 13. In accordance with this configuration, the substantial planar dimension of the second electrode 12C can be increased. The sensor chip 10 can also be manufactured readily, as compared to the configuration where the second electrode 12 and the attachment 13B are formed individually.

Figure 23A:
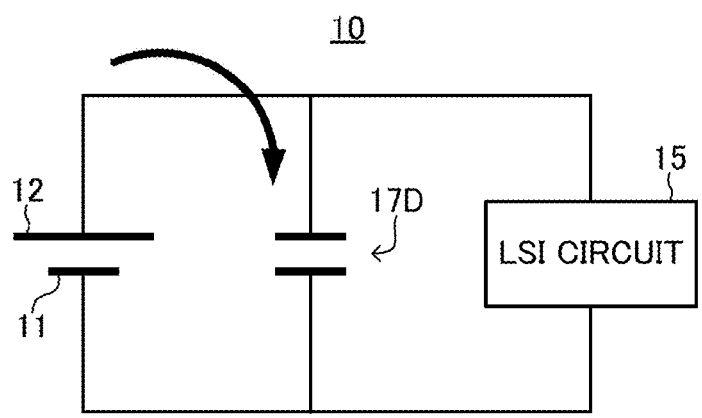
FIGS. 23A and 23B are block diagrams illustrating the configuration of another modification to the sensor chip in FIG. 1.
Figure 23B:
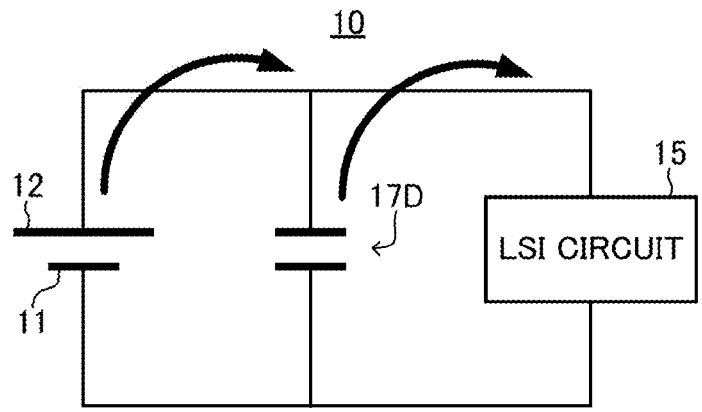

Alternatively, as shown in FIG. 23, the sensor chip 10 may include a capacitor 17D that is charged by the potential difference generated the first electrode 11 and the second electrode 12, and is capable of supplying an electric power to the LSI circuit 15 upon being discharged. FIG. 23A shows the flow of a current while the capacitor 17D is being charged. FIG. 23B shows the flow of a current while the capacitor 17D is being discharged.

In this configuration, the sensor chip 10 may include a switch that switches the sensor chip 10 between a mode to charge the capacitor 17D and another mode to discharge the capacitor 17D. For example, the sensor chip 10 may be configured to switch the sensor chip 10 from the mode to charge the capacitor 17D to the mode to discharge the capacitor 17D, when a certain duration passes after the potential difference is started to be observed between the first electrode 11 and the second electrode 12.

In the meantime, it often requires a certain time until detection of the target substance becomes sufficiently reliable after the analyte DB is placed in contact with the first electrode 11 and the second electrode 12. This means that, without the capacitor 17D, generated electric power may be wasted until the detection of the target substance becomes sufficiently reliable after the analyte DB is placed in contact with the first electrode 11 and the second electrode 12. At the time when a sufficiently high accuracy to detect the target substance becomes achievable, a sufficient electric power may not be supplied to the LSI circuit 15.

In the sensor chip 10 provided with the capacitor 17D, otherwise wasted electric power is stored in the capacitor 17D. As a result, the LSI circuit 15 can be driven in a reliable manner once a sufficiently high accuracy to detect the target substance becomes achievable.

Figure 24:
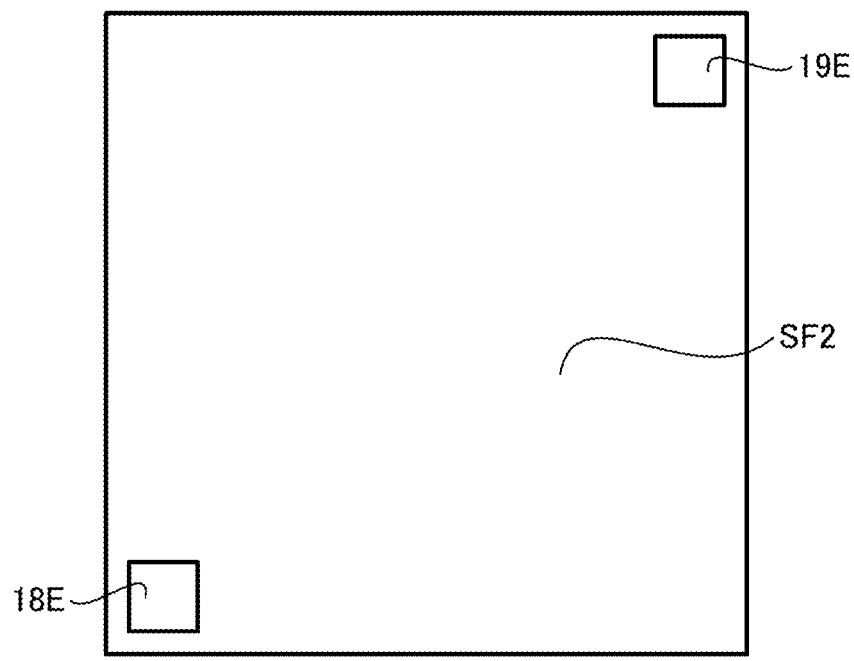
FIG. 24 is a back view illustrating the configuration of another modification to the sensor chip in FIG. 1.

Alternatively, as shown in FIG. 24, in place of the third electrode 18 and the fourth electrode 19, the sensor chip 10 may include a third electrode 18E and a fourth electrode 19E. The third electrode 18E and the fourth electrode 19E are exposed from the sensor chip 10 at the second surface SF2, instead of being exposed at the first surface SF1. In this configuration, the first electrode 11 and the second electrode 12 preferably do not have a notch 11b and a notch 12b, respectively.

Figure 25:
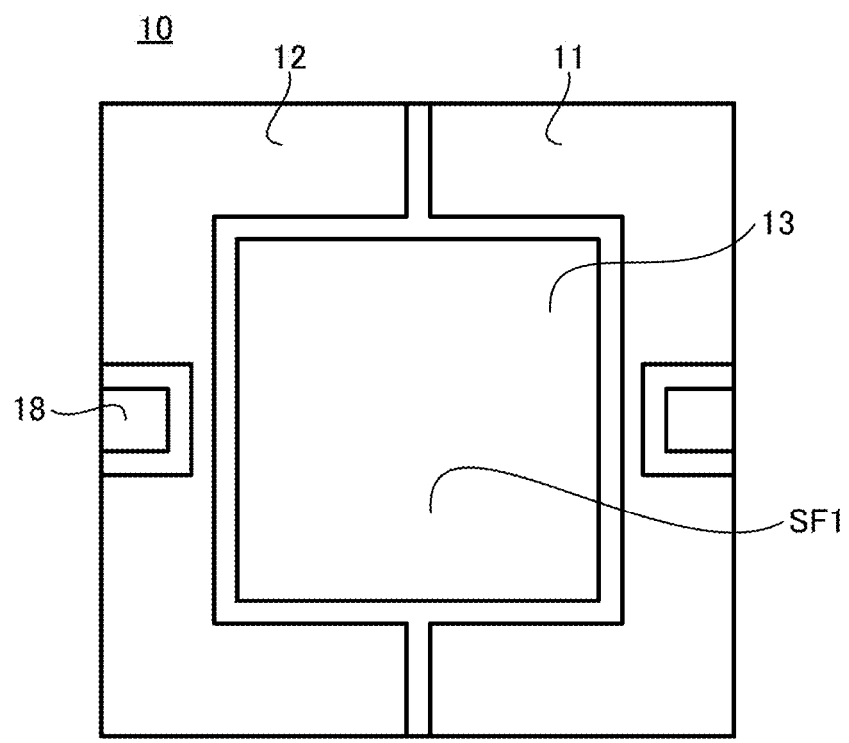
FIG. 25 is a front view illustrating the configuration of another modification to the sensor chip in FIG. 1.

Alternatively, as shown in FIG. 25, in the front view of the sensor chip 10, the third electrode 18 may be located in the vicinity of the center of a first side of the sensor chip 10, and the fourth electrode 19 may be located in the vicinity of the center of a second side of the sensor chip 10. The first and second sides are parallel to each other.

Alternatively, the sensor chip 10 may not include a third electrode 18 and a fourth electrode 19. In such a configuration, the sensor chip 10 outputs an electrical signal indicative of the detected count of antigens AG, via the first electrode 11 and the second electrode 12.

In accordance with this configuration, the sensor chip 10 can be manufactured more readily, as compared to a structure having the third electrode 18 and the fourth electrode 19.

[Second Embodiment]

Next, a detection system of a second embodiment will be described. The detection system of the second embodiment is different from the detection system of the first embodiment in that, in place of electrical signals, optical signals are used to conduct results of detections from a sensor chip to an obtainment unit. The detection system of the second embodiment will be described, focusing on the differences from the first embodiment. In the following descriptions of the second embodiment, like reference symbols refer to elements that are similar to or the same as those of the first embodiment.

Figure 26:
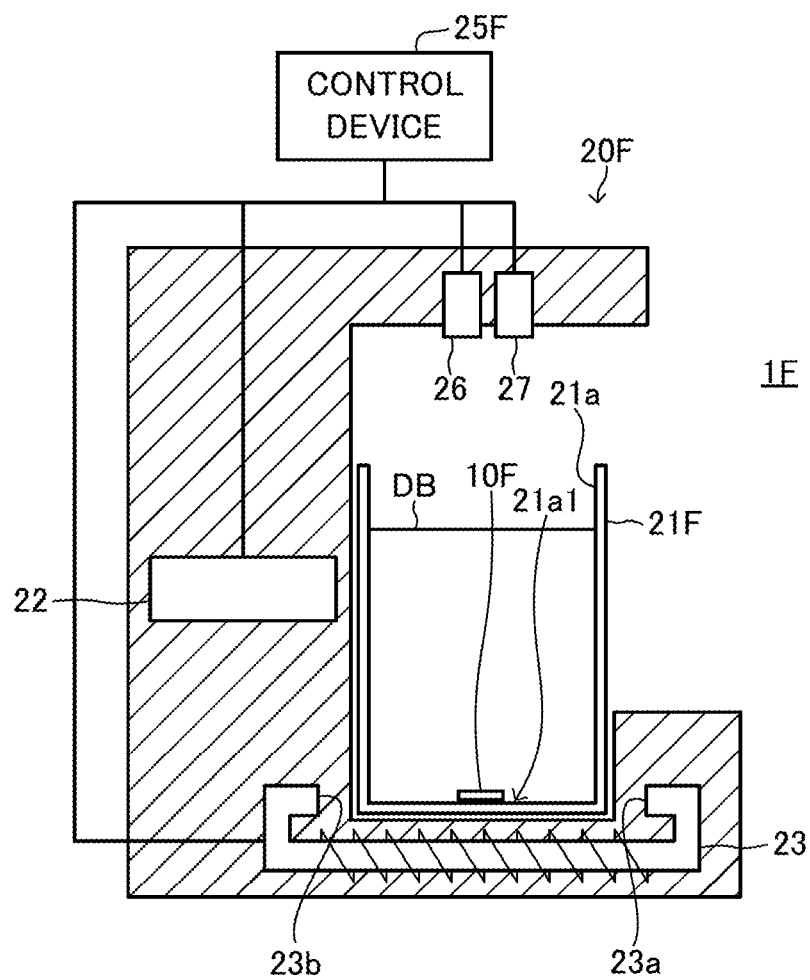
FIG. 26 is a diagram illustrating the configuration of the detection system of the second embodiment.

Referring to FIG. 26, a detection system of the second embodiment 1F includes a sensor chip 10F and an obtainment unit 20F.

Figure 27:
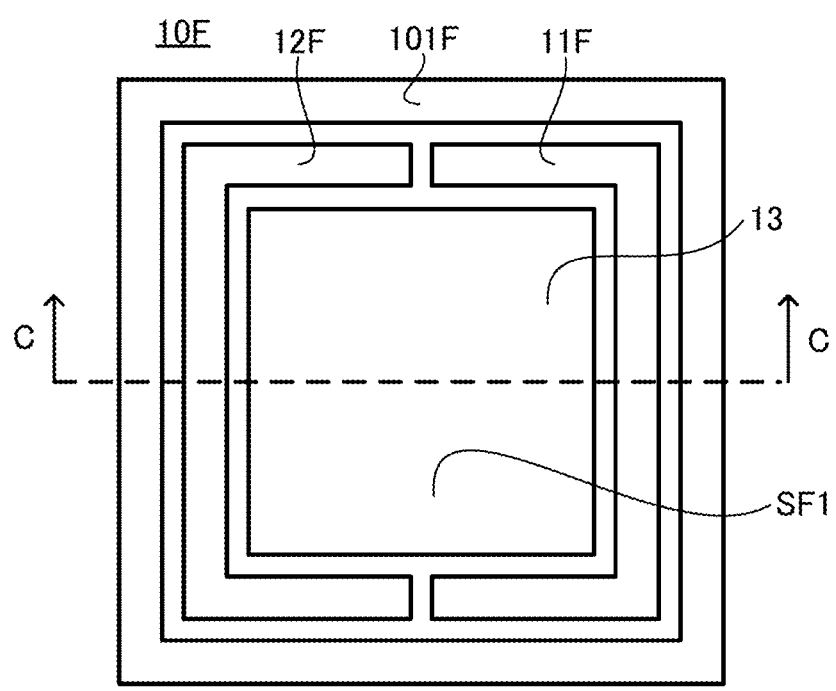
FIG. 27 is a front view illustrating the configuration of the sensor chip in FIG. 26.
Figure 28:
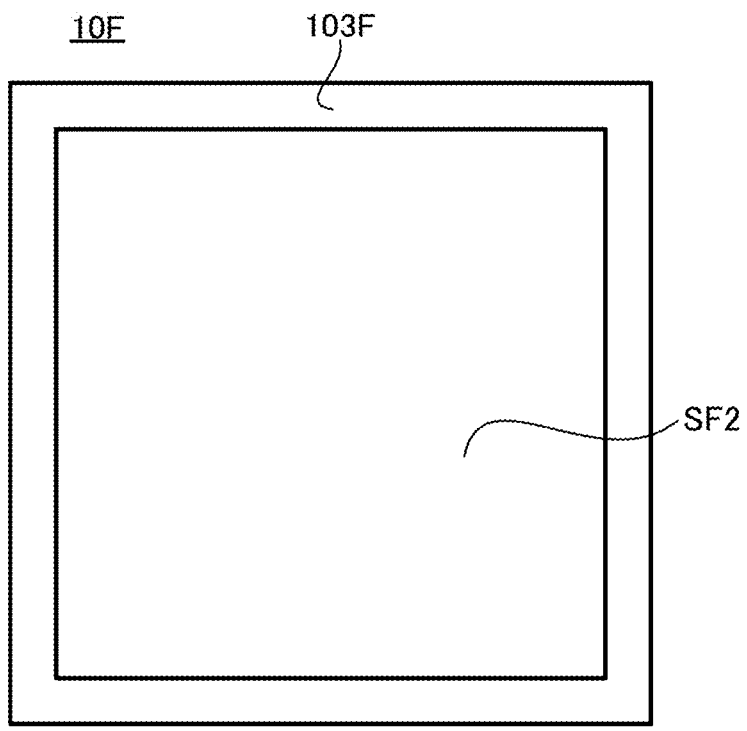
FIG. 28 is a back view illustrating the configuration of the sensor chip in FIG. 26.
Figure 29:
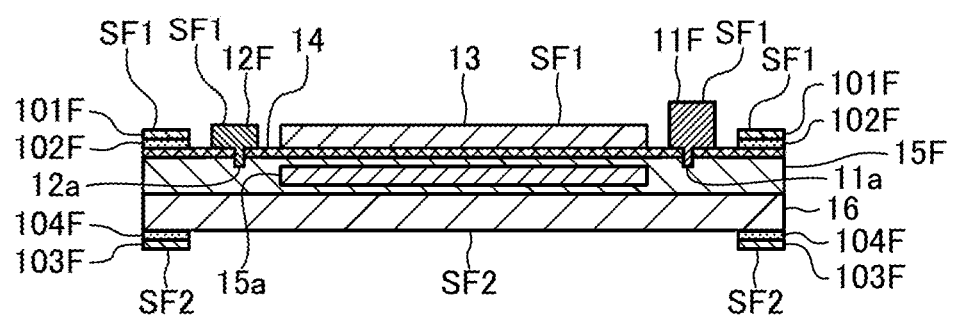
FIG. 29 is a cross-sectional view taken along Line C-C in FIG. 27.

FIG. 27 shows the sensor chip 10F viewed from the first surface SF1 in the thickness direction. FIG. 28 shows the sensor chip 10F viewed from the second surface SF2 in the thickness direction. FIG. 29 is a cross-sectional view of the sensor chip 10F taken along Line C-C in FIG. 27.

A shown in FIGS. 27-29, the sensor chip 10F includes a first electrode 11F, a second electrode 12F, an attachment 13, an insulator 14, an LSI circuit 15F, a substrate 16, a first shutter layer 101F, a first reflection layer 102F, a second shutter layer 103F, and a second reflection layer 104F.

The first reflection layer 102F and the second reflection layer 104F both reflect light. In the present example, the first reflection layer 102F and the second reflection layer 104F are retroreflectors. In other words, the first reflection layer 102F and the second reflection layer 104F reflect light incoming in a certain direction back to the direction opposite to the incoming direction.

The first reflection layer 102F stacks on the insulator 14, at the surface oppose to the LSI circuit 15F relative to the insulator 14. The second reflection layer 104F stacks on the substrate 16 at the surface oppose to the LSI circuit 15F relative to the substrate 16.

The first shutter layer 101F and the second shutter layer 103F each include a pair of transparent electrodes, and a liquid crystal sandwiched between the pair of transparent electrodes. The first shutter layer 101F and the second shutter layer 103F each are switched between a mode to allow passage of light and a mode to block the passage of the light, in response to a voltage applied across the respective transparent electrodes.

The first shutter layer 101F stacks on the first reflection layer 102F, at the surface oppose to the insulator 14 relative to the first reflection layer 102F. As a result, the first shutter layer 101F forms the first surface SF1 of the pair of surfaces of the sensor chip 10. In other words, the first shutter layer 101F is exposed from the sensor chip 10F at the first surface SF1.

The second shutter layer 103F stacks on the second reflection layer 104F, at the surface opposite to the substrate 16 relative to the second reflection layer 104F. As a result, the second shutter layer 103F forms the second surface SF2 of the pair of surfaces of the sensor chip 10. In other words, the second shutter layer 103F is exposed from the sensor chip 10F at the second surface SF2.

Referring to FIG. 27, the first shutter layer 101F has a predetermined width and is formed around the periphery of the sensor chip 10F, in the front view of the sensor chip 10F. The first reflection layer 102F has the same shape as that of the first shutter layer 101F, in the front view of the sensor chip 10F. In the front view of the sensor chip 10F, the centroid of the first reflection layer 102F coincides with the centroid of the first shutter layer 101F.

In the front view of the sensor chip 10F, the first shutter layer 101F, the first electrode 11F, the second electrode 12F, and the attachment 13 are spaced apart at a certain distance.

Referring to FIG. 28, the second shutter layer 103F has a predetermined width and is formed around the periphery of the sensor chip 10F, in the front view of the sensor chip 10F. The second reflection layer 104F has the same shape as that of the second shutter layer 103F, in the front view of the sensor chip 10F. In the front view of the sensor chip 10F, the centroid the second reflection layer 104F coincides with the centroid of the second shutter layer 103F.

Alternatively, the second shutter layer 103F and the second reflection layer 104F may have the same shape as that of the sensor chip 10F, in the front view of the sensor chip 10F. In such a configuration, the second shutter layer 103F forms the entire second surface SF2 of the pair of surfaces of the sensor chip 10.

Figure 30A:
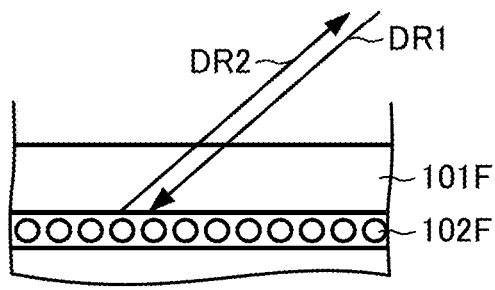
FIGS. 30A and 30B are schematic diagrams illustrating the functions of the shutter and reflection layers in FIG. 29.

In this configuration, as shown in FIG. 30A, when the first shutter layer 101F is controlled to the mode to allow passage of light, light entering to the sensor chip 10F in Direction DR1 is reflected back to Direction DR2 opposite to the incoming direction.

Figure 30B:
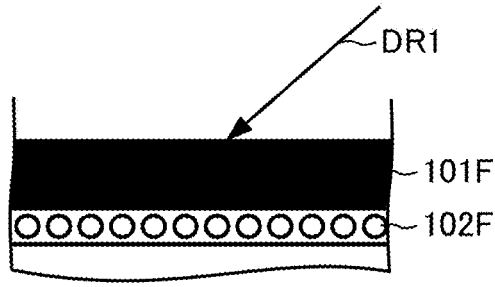

In contrast, as shown in FIG. 30B, the first shutter layer 101F is controlled to the mode to block the passage of light, light entering to the sensor chip 10F is not reflected.

Figure 31:
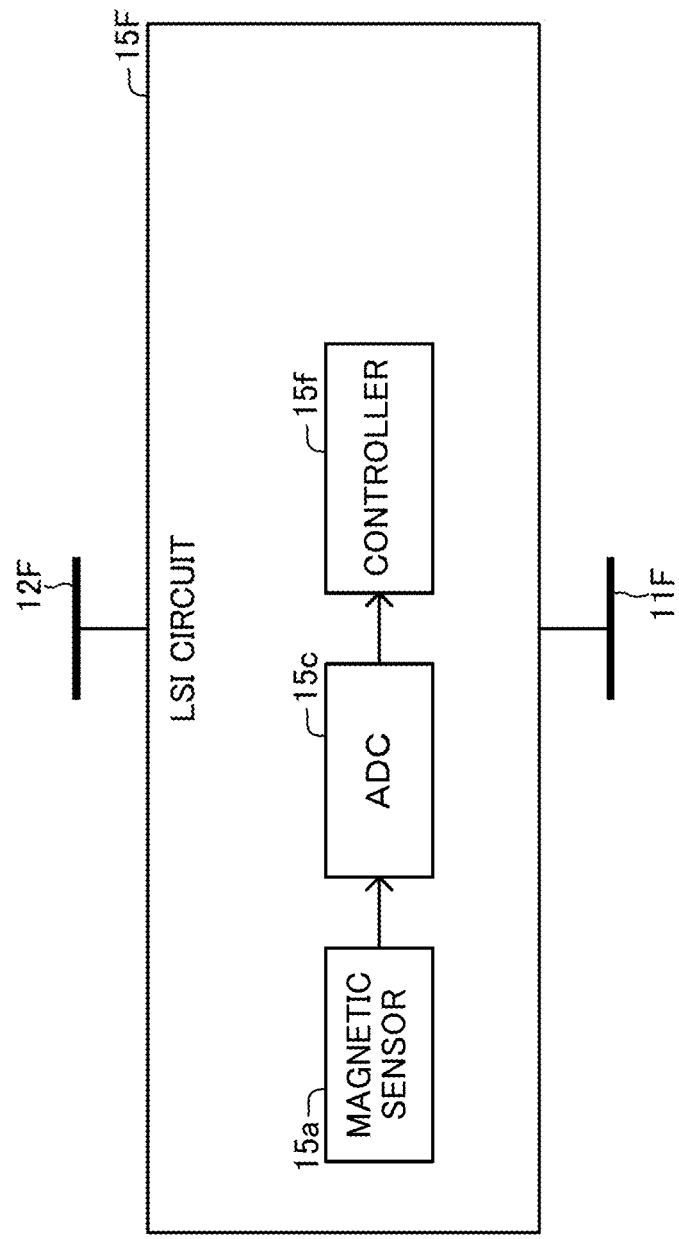
FIG. 31 is a block diagram illustrating the function of the LSI circuit in FIG. 29.

The LSI circuit 15F will be described. Referring to FIG. 31, the LSI circuit 15F includes a magnetic sensor 15a, an ADC 15c, and a controller 15f. The ADC 15c, and the controller 15f collectively represent an example of an output circuit. The controller 15f represents an example of a controller.

The controller 15f controls modes of the first shutter layer 101F and the second shutter layer 103F, in accordance with a signal converted by the ADC 15c. In the present example, the controller 15f controls the first shutter layer 101F and the second shutter layer 103F to the mode to allow passage of light in the duration when the converted signal assumes a value representing "1", while controlling the first shutter layer 101F and the second shutter layer 103F to the mode to block the passage of light in the duration when the converted signal assumes a value representing "0".

In other words, the controller 15f switches the modes of the first shutter layer 101F and the second shutter layer 103F, at timing associated with the result of the detection of the antigens AG contained in the analyte DB.

Alternatively, the controller 15f can control the modes of the first shutter layer 101F and the second shutter layer 103F, in the reversed manner.

Referring back to FIG. 26, the obtainment unit 20F includes a cell 21F, a first magnet 22, a second magnet 23, a control device 25F, a light source 26, and a photo-detector 27. The cell 21F represents an example of a container. The control device 25F and the photo-detector 27 collectively represent an example of a detector.

The cell 21F is detachably attached to the obtainment unit 20F. In the present example, the cell 21F is a disposable container. For example, the cell 21F is a cup made of paper or plastic.

The light source 26 emits light toward the bottom 21a1 of the inner wall 21a, while the cell 21F is attached to the obtainment unit 20F. For example, the light source 26 is a light emitting diode. In this configuration, the sensor chip 10F is disposed in the cell 21F, and the sensor chip 10F is irradiated with the light emitted from the light source 26. Alternatively, the light source 26 may be a semiconductor laser (e.g., laser diode).

The photo-detector 27 is located in the vicinity of the light source 26. When the cell 21F containing the sensor chip 10F is attached to the obtainment unit 20F, the photo-detector 27 detects light that is emitted from the light source 26 and reflected by the sensor chip 10F.

The control device 25F obtains the result of the detection of the antigens AG contained in the analyte DB from the sensor chip 10F, based on light that is reflected, and then detected by the photo-detector 27.

The detection system 1F functions in the manner similar to the detection system of the first embodiment 1, except that the detection system 1F conducts, in place of an electrical signal, an optical signal represented by light that is emitted from the light source 26 and reflected by the sensor chip 10F, from the sensor chip 10F to the obtainment unit 20F.

As described above, the sensor chip 10F of the second embodiment has advantages and effects similar to those of the sensor chip 10 of the first embodiment.

Additionally, the sensor chip 10F of the second embodiment includes the shutter layers 101F and 103F that form the surfaces SF1 and SF2 of the sensor chip 10F, shutter layers 101F and 103F being switched between a mode to allow passage of light and a mode to block the passage of the light. The sensor chip 10F further includes the reflection layers 102F and 104F that reflect the light, the reflection layers 102F and 104F being stacked on the shutter layers 101F and 103F at surfaces opposite to the surfaces SF1 and SF2 relative to the shutter layers 101F and 103. Furthermore, the controller 15f switches the modes of the shutter layers 101F and 103F at timing associated with the result of the detection of the antigens AG contained in the analyte DB.

In accordance with this configuration, when the sensor chip 10F is irradiated with light, an optical signal that represents the result of the detection in the form of absence or presence of reflected light, can be detected. As a result, an optical signal representing the result of the detection can be conducted to the obtainment unit 20F external to the sensor chip 10F, without requiring any antenna coil. The planar dimension of the sensor chip 10F hence can be reduced, as compared to that of a sensor chip having an antenna coil.

Alternatively, in the sensor chip 10F, the second electrode 12F may be formed integrally with the attachment 13. Alternatively, the sensor chip 10F may be formed such that the first electrode 11F is exposed from the sensor chip 10F, not at the first surface SF1, but at the second surface SF2.

Alternatively, the sensor chip 10F may include either one of: the first shutter layer 101F and the first reflection layer 102F; and the second shutter layer 103F and the second reflection layer 104F.

Alternatively, after the magnetized particles MP are attached to the attachment 13 while the cell 21F is detached from the obtainment unit 20F, the cell 21F may be attached to the obtainment unit 20F. In this configuration, while the cell 21F is detached from the obtainment unit 20F, the first magnet 22 attracts no magnetized particles MP. Hence, the first magnet 22 can be maintained at the position near the inner wall 21a even before the magnetized particles MP are attached to the attachment 13. In this configuration, the driving mechanism for the first magnet 22 can be omitted from the obtainment unit 20F.

The present invention is not limited to the embodiments as set forth above. For example, various modifications that may be conceived of by those skilled in the art may be made to the above-described embodiments, without departing from the spirit of the present invention. For example, the embodiments and modification thereto may be combined as alternative modifications to the embodiments, without departing from the spirit of the present invention.

What is claimed is:

1. A sensor chip comprising:
   first and second electrodes that are exposed from the sensor chip and are made from materials different from each other;
   a detection circuit that detects a target substance included in an analyte, the detection circuit being driven by a potential difference between the first and second electrodes, the potential difference being generated by an oxidation at the first electrode and a reduction at the second electrode while the analyte contacts the first and second electrodes, the analyte including an electrolyte.

2. The sensor chip according to claim 1, wherein the sensor chip further comprises first antibody having an affinity for antigen that is the target substance, and
   the detection circuit comprises a magnetic sensor that detects at least one of magnetized particles including second antibody having an affinity for the antigen bound to the first antibody, having the second antibody and the antigen interposed therebetween.

3. The sensor chip according to claim 1, further comprising a capacitor that is charged by the potential difference, and is capable of supplying an electric power to the detection circuit upon being discharged.

4. The sensor chip according to claim 1, further comprising an output circuit that outputs a result of the detection by being driven by the potential difference.

5. The sensor chip according to claim 4, further comprising third and fourth electrodes,
   wherein the output circuit outputs, via the third and fourth electrodes, an electrical signal indicative of the result of the detection.

6. The sensor chip according to claim 4, wherein the output circuit outputs, via the first and second electrodes, an electrical signal indicative of the result of the detection.

7. The sensor chip according to claim 4, wherein the sensor chip further comprises:
   a shutter layer that forms a surface of the sensor chip, the shutter layer being switched between a mode to allow passage of light and a mode to block the passage of the light; and
   a reflection layer that reflects the light, the reflection layer being stacked on the shutter layer at a surface opposite to a surface of the shutter layer forming the surface of the sensor chip,
   wherein the output circuit comprises a controller that switches the mode of the shutter layer at timing associated with the result of the detection.

8. The sensor chip according to claim 1, wherein the sensor chip has a planer shape having a pair of surfaces which are parallel to each other, and
   the first and second electrodes are exposed from the sensor chip at a first surface of the pair of surfaces.

9. The sensor chip according to claim 1, wherein the sensor chip has a planer shape having a pair of surfaces which are parallel to each other,
   the first electrode is exposed from the sensor chip at a first surface of the pair of surfaces,
   the second electrode is exposed from the sensor chip at a second surface of the pair of surfaces.

10. The sensor chip according to claim 8, further comprising:
    first antibody having an affinity for antigen that is the target substance; and
    an attachment to which the first antibody is attached, the attachment being exposed from the sensor chip at the first surface and being integrated with the second electrode.

11. The sensor chip according to claim 9, further comprising:
    first antibody having an affinity for antigen that is the target substance; and
    an attachment to which the first antibody is attached, the attachment being exposed from the sensor chip at the second surface and being integrated with the second electrode.

12. The sensor chip according to claim 1, wherein the first electrode is made from zinc or magnesium.

13. A detection system comprising:
a sensor chip comprising:
first and second electrodes that are exposed from the sensor chip and are made from materials different from each other;
a detection circuit that detects a target substance included in an analyte, the detection circuit being driven by a potential difference between the first and second electrodes, the potential difference being generated by an oxidation at the first electrode and a reduction at the second electrode while the analyte contacts the first and second electrodes, the analyte including an electrolyte; and
an output circuit that outputs a result of the detection by being driven by the potential difference; and
an obtainment unit that obtains a result of the detection output from the sensor chip.

14. The detection system according to claim 13, wherein the sensor chip further comprises third and fourth electrodes,
the output circuit outputs, via the third and fourth electrodes, an electrical signal indicative of the result of the detection,
the obtainment unit further comprises:
a container that contains the analyte and the sensor chip included in the analyte, and comprises a plurality of electrodes contacting the contained analyte; and
a detector that detects a potential difference between electrodes of the plurality of electrodes, and
the obtainment unit obtains the result of the detection from the sensor chip based on the detected potential difference.

15. The detection system according to claim 13, wherein the output circuit outputs, via the first and second electrodes, an electrical signal indicative of the result of the detection,
the obtainment unit further comprises:
a container that contains the analyte and the sensor chip included in the analyte, and comprises a plurality of electrodes contacting the contained analyte; and
a detector that detects a potential difference between electrodes of the plurality of electrodes, and
the obtainment unit obtains the result of the detection from the sensor chip based on the detected potential difference.

16. The detection system according to claim 13, wherein the sensor chip further comprises:
a shutter layer that forms a surface of the sensor chip, the shutter layer being switched between a mode to allow passage of light and a mode to block the passage of the light; and
a reflection layer that reflects the light, the reflection layer being stacked on the shutter layer at a surface opposite to a surface of the shutter layer forming the surface of the sensor chip,
the output circuit comprises a controller that switches the mode of the shutter layer at timing associated with the result of the detection;
the obtainment unit further comprises:
a container that contains the analyte and the sensor chip included in the analyte; and
a light source that emits the light toward the contained sensor chip; and
a detector that detects light emitted from the light source and reflected by the sensor chip,
wherein the obtainment unit obtains the result of the detection from the sensor chip based on the reflected light that is detected.

17. A method of detecting a target substance in an analyte, comprising:
contacting first and second electrodes to the analyte including an electrolyte, the first and second electrodes being exposed from a sensor chip and being made from materials different from each other;
generating a potential difference between the first and second electrodes by an oxidation at the first electrode and a reduction at the second electrode; and
detecting, by a detection circuit that is comprised in the sensor chip and that is driven by the potential difference, the target substance included in the analyte by the sensor chip driven by the potential difference.

18. The method according to claim 17, further comprising outputting the result of the detection by the sensor chip driven by the potential difference.

19. The method according to claim 18, further comprising obtaining, by an obtainment unit, the result of the detection output from the sensor chip.

20. The method according to claim 17, further comprising:
adding magnetized particles including second antibody having an affinity for antigen that is the target substance, to the analyte;
causing the added magnetized particles to bind first antibody having an affinity for the antigen, having the second antibody and the antigen interposed therebetween, the first antibody being attached to the sensor chip;
attracting, by a first magnet, a part of the added magnetized particles that do not bind to the first antibody;
generating a magnetic field, by a second magnet having a pair of magnetic poles, a line connecting the magnetic poles being parallel to the sensor chip; and
detecting at least one of the magnetized particles bound to the first antibody by detecting the generated magnetic field by a magnetic sensor.

* * * * *